United States Patent
Banchereau et al.

(10) Patent No.: US 7,544,357 B2
(45) Date of Patent: Jun. 9, 2009

(54) METHODS FOR TREATING AUTOIMMUNE DISEASES IN A SUBJECT AND IN VITRO DIAGNOSTIC ASSAYS

(75) Inventors: Jacques F. Banchereau, Dallas, TX (US); Anna Karolina Palucka, Dallas, TX (US); Patrick Blanco, Talence (FR)

(73) Assignee: Baylor Research Institute, Dallas, TX (US)

( * ) Notice: Subject to any disclaimer, the term of this patent is extended or adjusted under 35 U.S.C. 154(b) by 0 days.

(21) Appl. No.: 10/466,023

(22) PCT Filed: Jan. 8, 2002

(86) PCT No.: PCT/US02/00343

§ 371 (c)(1),
(2), (4) Date: Jul. 7, 2003

(87) PCT Pub. No.: WO02/067760

PCT Pub. Date: Sep. 6, 2002

(65) Prior Publication Data

US 2004/0067232 A1    Apr. 8, 2004

Related U.S. Application Data

(60) Provisional application No. 60/260,541, filed on Jan. 9, 2001.

(51) Int. Cl.
*A61K 39/395* (2006.01)
*C12P 21/08* (2006.01)
*C07K 16/18* (2006.01)
*C07K 16/22* (2006.01)
*C07K 16/24* (2006.01)

(52) U.S. Cl. .............. 424/130.1; 424/131.1; 424/133.1; 424/136.1; 424/145.1; 530/387.1; 530/387.2; 530/388.1; 530/388.23; 530/388.24

(58) Field of Classification Search .............. 424/131.1, 424/133.1, 141.1, 145.1
See application file for complete search history.

(56) References Cited

U.S. PATENT DOCUMENTS

| | | | |
|---|---|---|---|
| 4,362,155 A | 12/1982 | Skurkovich | |
| 4,414,150 A | 11/1983 | Goeddel | |
| 4,423,147 A | 12/1983 | Secher et al. | |
| 4,456,748 A | 6/1984 | Goeddel | |
| 4,474,754 A | 10/1984 | Shimizu et al. | |
| 4,534,906 A | 8/1985 | Johnston | |
| 4,605,394 A | 8/1986 | Skurkovich | |
| 4,650,674 A | 3/1987 | Aggarwal et al. | |
| 4,678,751 A | 7/1987 | Goeddel | |
| 4,727,138 A | 2/1988 | Goeddel et al. | |
| 4,762,791 A | 8/1988 | Goeddel et al. | |
| 4,824,432 A | 4/1989 | Skurkovich et al. | |
| 4,828,830 A | 5/1989 | Wong | |
| 4,851,219 A | 7/1989 | Sherwin | |
| 4,902,618 A | 2/1990 | Berg | |
| 4,925,793 A | 5/1990 | Goeddel et al. | |
| 4,944,941 A | 7/1990 | Ammann | |
| 4,973,556 A | 11/1990 | Bove et al. | |
| 4,987,071 A | 1/1991 | Cech et al. | |
| 5,055,289 A | 10/1991 | Frincke et al. | |
| 5,082,658 A | 1/1992 | Palladino | |
| 5,096,705 A | 3/1992 | Goeddel et al. | |
| 5,168,053 A | 12/1992 | Altman et al. | |
| 5,196,323 A | 3/1993 | Bodo et al. | |
| 5,227,158 A | 7/1993 | Jardieu | |
| 5,248,499 A | 9/1993 | Czarniecki et al. | |
| 5,254,678 A | 10/1993 | Haseloff et al. | |
| 5,460,811 A | 10/1995 | Goeddel et al. | |
| 5,554,512 A | 9/1996 | Lyman et al. | |
| 5,582,824 A | 12/1996 | Goeddel et al. | |
| 5,595,888 A | 1/1997 | Gray et al. | |
| 5,827,694 A | 10/1998 | Capon et al. | |
| 5,831,023 A | 11/1998 | Capon et al. | |
| 5,843,423 A | 12/1998 | Lyman et al. | |
| 5,886,153 A | 3/1999 | Mogensen et al. | |
| 5,888,511 A * | 3/1999 | Skurkovich et al. | ...... 424/145.1 |
| 5,889,151 A | 3/1999 | Mogensen et al. | |
| 5,919,452 A | 7/1999 | Le et al. | |
| 5,919,453 A | 7/1999 | Benoit et al. | |

(Continued)

FOREIGN PATENT DOCUMENTS

| | | |
|---|---|---|
| EP | 0254647 | 1/1988 |
| EP | 0 325 471 A1 | 7/1989 |
| EP | 360257 | 3/1990 |
| EP | 0 627 487 A2 | 7/1997 |
| WO | WO 93/04699 * | 3/1993 |
| WO | WO 95/07716 | 3/1995 |
| WO | WO 97/41229 | 11/1997 |
| WO | WO 01/49851 | 7/2001 |
| WO | WO 01/54721 | 8/2001 |
| WO | WO 2004/094473 | 11/2004 |
| WO | WO 2005/059106 | 6/2005 |
| WO | WO 2006/037247 | 4/2006 |

OTHER PUBLICATIONS

Ngo et al.,The Protein Folding Problem and Tertiary Structure Prediction, pp. 491-495, 1994.*

(Continued)

*Primary Examiner*—Phuong Huynh
(74) *Attorney, Agent, or Firm*—Brinks Hofer Gilson & Lione

(57) ABSTRACT

The invention provides a method for treating an autoimmune disease in a subject by administering an interferon antagonist and a Flt3 ligand (Flt3L) antagonist. The invention also provides compositions containing one or more interferon antagonists, and one or more Flt3L antagonists, an in vitro assay for determining a subject's risk for developing an autoimmune disease, and kits for use, inter alia, with the assay.

6 Claims, 19 Drawing Sheets

U.S. PATENT DOCUMENTS

| | | | |
|---|---|---|---|
| 5,959,085 | A | 9/1999 | Garrone et al. |
| 6,136,309 | A | 10/2000 | Novick et al. |
| 6,200,780 | B1 | 3/2001 | Chen et al. |
| 6,274,378 | B1 | 8/2001 | Steinman et al. |
| 6,291,661 | B1 * | 9/2001 | Graddis et al. ............. 536/23.4 |
| 6,299,869 | B1 | 10/2001 | Chen et al. |
| 6,299,877 | B1 | 10/2001 | Chen et al. |
| 6,300,475 | B1 | 10/2001 | Chen et al. |
| 6,333,032 | B1 | 12/2001 | Skurkovich et al. |
| 6,458,932 | B1 | 10/2002 | Novick et al. |
| 6,475,983 | B1 | 11/2002 | Eid et al. |
| 6,630,143 | B1 | 10/2003 | Lyman et al. |
| 6,660,523 | B2 * | 12/2003 | Blom et al. ................. 435/377 |
| 6,673,908 | B1 | 1/2004 | Stanton, Jr. |
| 6,713,609 | B1 | 3/2004 | Chuntharapai |
| 6,787,634 | B2 | 9/2004 | Benoit et al. |
| 7,087,726 | B2 | 8/2006 | Chuntharapai et al. |
| 7,179,465 | B2 | 2/2007 | Benoit et al. |
| 2002/0160974 | A1 | 10/2002 | Banchereau et al. |
| 2003/0018174 | A1 | 1/2003 | Kim et al. |
| 2003/0021764 | A1 | 1/2003 | Maroun |
| 2003/0147889 | A1 | 8/2003 | Tovey |
| 2003/0166228 | A1 | 9/2003 | Chuntharapai |
| 2004/0132139 | A1 | 7/2004 | Escary |
| 2004/0191840 | A1 | 9/2004 | Benoit et al. |
| 2005/0013799 | A1 | 1/2005 | Skurkovich et al. |
| 2005/0013800 | A1 | 1/2005 | Skurkovich et al. |
| 2005/0013813 | A1 | 1/2005 | Maroun |
| 2007/0014724 | A1 | 1/2007 | Witte et al. |

OTHER PUBLICATIONS

Mason et al, Molecular Endocrinology 8(3): 325-332, 1994.*
Hron et al, J Immunology 173: 2134-2142, 2004.*
Van Noort et al, International Review of Cytology 178: 127-205, 1998.*
Paquette et al, J Leukocyte Biology 64: 358-367, Sep. 1998.*
Santini et al, J Exp Med 191(10): 1777-1788, May 15, 2000.*
Blom, et al. (2000) "Generation of interferon aplpha-producing Predendritic Cell (Pre-DC)2 from Human CD34 Hematopoietic Stem Cells" *Journal of Experimental Medicine*, v. 192 (12): 1785-1795.
Pulendran et al. (2000) "Flt3-Ligand and Granulocyte Colony Stimulating Factor Mobilize Distinct Human Dendritic Cell Subsets in Vivo" *Journal of Immunology*. 165(1): 566-572.
Gill et al. (2002) "Blood dendritic cells and DC-poietins in systemic lupus erythematosus" *Human Immunology*, v. 63 (12): 1172-1180.
Blanco, P. et al. "Induction of Dendritic Cell Differentiation by IFN-a in Systemic Lupus Erythematosus". Nov. 16, 2001, vol. 294, Science, pp. 1540-1543.
Brod, S. et al. "Ingested IFN-α Preserves Residual β Cell Function in Type 1 Diabetes". Journal of Interferon And Cytokine Research 21:1021-1030 (2001) Mary Ann Liebert, Inc.
Prud'homme, G. et al: "Gene therapy of autoimmune diseases with vectors encoding regulatory cytokines or inflammatory cytokine inhibitors". The Journal of Gene Medicine, J Gene Med 2000; 2: 222-232.
Shou-Nee, S. et al. "Serum interferon in systemic lupus erythematosus". *British Journal of Dermatology* (1987) 117, 155-159.
Suit, B.E. et al: "Detection of anti-interferon antibodies in systemic lupus erythematosus". *Clinical and Experimental Rheumatology* 1: 133-135, 1983.
Wang, S. et al. "A Unique Combination of Inflammatory Cytokines Enhances Apoptosis of Thyroid Follicular Cells and Transforms Nondestructive to Destructive Thyroiditis in Experimental Autoimmune Thyroiditis". The Journal of Immunology, 2002, 168: 2470-2474.
Wussow, von P. et al: "Presence of interferon and anti-interferon in patients with systemic lupus erythematosus". Rheumatol International (1988) 8: 225-230.
Ytterberg, S. et al: "Serum Interferon Levels In Patients With Systemic Lupus Erythematosus". Arthritis and Rheumatism, vol. 25, No. 4 (Apr. 1982).
Huang, Xiaojian et al. Islet Expression of Interferon-α Precedes Diabetes in both the BB Rat and Streptozotocin-Treated Mice. Immunity 1:469-478 (1994).
Soos, Jeanne M. et al. Oral feeding of interferon T can prevent the acute and chronic relapsing forms of experimental allergic encephalomyelitis. Journal of Neuroimmunology 75:43-50 (1997).
PCT Notification of Transmittal of International Search Report or The Declaration for PCT/US02/00343, dated Dec. 4, 2002.
Banchereau, J.; Brier, F.; Caux, C.; Davoust, J.; Lebecque, S.; Liu, Y.J. "Immunology of Dendritic Cells" *Annual Review of Immunology* vol. 18, pp. 767-811 (2000).
Blazar, B.R.; McKenna, H.J.; Panoskaltsis-Mortari, A.; Taylor, P.A.; "Flt3 Ligand (FL) Treatment of Murine Donors Does Not Modify Graft-Versus-Host Disease (GVHD) But FL Treatment of Recipients Post-Bone Marrow Transplantation Accelerates GVHD Lethality" *Biology of Blood and Marrow Transplantation* vol. 7, Issue 4, pp. 197-207 (2001).
Chakrabarti, D.; Hultgren, B.; Stewart, T.A. "IFN-α Induces Autoimmune T Cells Through the Induction of Intracellular Adhesion Molecule-1 and B7.2" *Journal of Immunology* vol. 157, pp. 522-528 (1996).
Chuntharapai, A.; Lai, J.; Huang, X.; Gibbs, V.; Kim, K.J.; Presta, L.G.; Stewart, T.A. "Characterization and Humanization of Monoclonal Antibody That Neutralizes Human Leukocyte Interferon: a Candidate Therapeutic for IDDM and SLE" *Cytokine* vol. 15, No. 5.
Panem, Sandra, et al., "Antibodies to α-Interferon in a Patient with Systemic Lupus Erythematosus", J. Immunology, 1982, p. 1-3, vol. 129, No. 1.
Alkan and Braun (1986) *Ciba Found. Symp.* 119; 264-278, entitled "Epitope Mapping of Human Recombinant Interferon alpha Molecules by Monoclonal Antibodies."
Baechler et al. (2003) *Proc. Nat'l. Acad. Sci. USA* 100(5): 2610-2615, entitled "Interferon-inducible gene expression signature in peripheral blood cells of patients with severe lupus."
Banchereau et al. (2004) *Immunity* 20(5): 539-50, entitled "Autoimmunity through cytokine-induced dendritic cell activation."
Båve et al. (2003) *J. Immunol.* 171: 3296-3302, entitled "FcγRlla is expressed on natural IFN-α-producing cells (plasmacytoid dendritic cells) and is required for the IFN-α production induced by apoptotic cells combined with lupus IgG."
Berg (1984) *J. Interferon Res.* 4(4): 481-491, entitled "Identification, production, and characterization of murine monoclonal antibody (LO-22) recognizing 12 native species of human alpha interferon."
Björck (2004) *J. Immunol.* 172(9): 5396-5404, entitled "Dendritic cells exposed to herpes simplex virus in vivo do not produce IFN-alpha after rechallenge with virus in vitro and exhibit decreased T cell alloreactivity."
Blank et al. (1999) *Eur. J. Biochem.* 265(1): 11-19, entitled "Identification of a linear epitope of interferon-alpha 2b recognized by neutralizing monoclonal antibodies."
Blomberg et al. (2003) *Arthritis Rheum.* 48(9): 2524-32, entitled "Expression of the markers BDCA-2 and BDCA-4 and production of interferon-alpha by plasmacytoid dendritic cells in systemic lupus erythematosus."
Braun et al. (2003) *J. Autoimmun.* 20(1): 15-25, entitled "Type I interferon controls the onset and severity of autoimmune of autoimmune manifestations in Ipr mice."
Crow and Kirou (2004) *Curr. Opin. Rheumatol.* 16(5): 541-47, entitled "Interferon-alpha in systemic lupus erythematosus."
Crow (2003) *Arthritis Rheum.* 48(9): 2396-2401, entitled, "Interferon-alpha: a new target for therapy in systemic lupus erythematosus?"
Devendra and Eisenbarth (2004) *Clin. Immunol.* 111(3): 225-233, entitled "Interferon alpha—a potential link in the pathogenesis of viral-induced type I diabetes and autoimmunity."
Exley et al. (1984) *J. Gen. Virol.* 65 (12): 2277-2280, entitled "A comparison of the neutralizing properties of monoclonal and polyclonal antibodies to human interferon alpha."

Files et al. (1998) *J. Interferon Cytokine Res.* 18(12): 1019-24, entitled "A novel sensitive and selective bioassay for human type I interferons."

Fish et al. (1989) *J. Interferon Res.* 9(1): 97-114, entitled "The role of three domains in the biological activity of human interferon-alpha."

Foster et al. (2004) *J. Immunol.* 173(3): 1663-70, entitled "IFN-alpha subtypes differentially affect human T cell motility."

Green et al. (2004) *Cytokine* 26(5): 209-16, entitled "IgG-derived Fc down-regulates virus-induced plasmacytoid dendritic cell (pDC) IFNα production."

Gringeri et al. (1999) *J. AIDS Hum. Retrovirol.* 20(4): 358-70, entitled "Active anti-interferon-alpha immunization: a European-Israeli, randomized, double-blind, placebo-controlled clinical trial in 242 HIV-1-infected patients (the EURIS study)."

Gringeri et al. (1996) *J. AIDS Hum. Retrovirol.* 13(1): 55-67, entitled "Absence of clinical, virological, and immunological signs of progression in HIV-1-infected patients receiving active anti-interferon-alpha immunization: a 30-month follow-up report."

Gringeri et al. (1995) *Cell. Mol. Biol.* (Noisy-le-grand) 41(3): 381-87, entitled "Anti-alpha interferon immunization: safety and immunogenicity in asymptomatic HIV positive patients at high risk of disease progression."

Huang et al. (1994) *Immunity* 1: 469-478, entitled "Islet Expression of IFN-α Precedes Diabetes in Both the BB Rat and Streptozotocin-treated Mice".

Hussain et al. (1997) *J. Interferon Cytokine Res.* 17(9): 559-66, entitled "Both variant forms of interferon-alpha4 gene (IFNA4a and IFNA4b) are present in the human population."

Isenberg and Leckie (2002) *Scand. J. Rheumatol.* 31(4): 187-91, entitled "Biological treatments for systemic lupus erythematosus."

Kirou et al. (2004) *Arthritis & Rheumatism* 50(12): 3958-3967, entitled "Coordinate overexpression on interferon-alpha-induced genes in systemic lupus erythematosus."

Mohty et al. (2003) *J. Immunol.* 171(7): 3385-93, entitled "IFN-alpha skews monocyte differentiation into Toll-like receptor 7-expressing dendritic cells with potent functional activities."

Morser et al. (1981) *J. Gen. Virol.* 53(2): 257-65, entitled "Production and screening of cell hybrids producing a monoclonal antibody to human interferon-alpha."

Noll et al. (1989) *Biomed. Biochim. Acta* 48(1): 165-76, entitled "Production and characterization of four monoclonal antibodies specific for human interferon-alpha-1 and -alpha-2."

Overall and Hertzog (1992) *Mol. Immunol.* 29(3): 391-99, entitled "Functional analysis of interferon-alpha subtypes using monoclonal antibodies to interferon-alpha4a-subtype reactivity, neutralisation of biological activities and epitope analysis."

Reyes and Klimpel (1987) *Transplantation* 43(3): 412-416, entitled "Interferon alpha/beta synthesis during acute graft-versus-host disease."

Rönnblom et al. (2003) *Autoimmunity* 36(8): 463-472, entitled "Role of Natural Interferon-α Producing Cells (Plasmacytoid Dendritic Cells) in Autoimmunity."

Rönnblom and Alm (2001) *Trends Immunol.* 22(8): 427-31, entitled "An etiopathogenic role for the type I IFN system in SLE."

Rönnblom and Alm (2001) *J. Exp. Med.* 194(12): F59-63, entitled "A pivotal role for the natural interferon alpha-producing cells (plasmacytoid dendritic cells) in the pathogenesis of lupus."

Santiago-Raber et al. (2003) *J. Exp. Med.* 197(6): 777-88, entitled "Type-I interferon receptor deficiency reduces lupus-like disease in NZB mice."

Schattner et al., (1988) "Review: Interferons and autoimmunity". Am. J. Med. Sci. 295:532-544.

Skurkovich et al., (1977). Lymphocytes' cytotoxicity towards cells of human lymphoblastoid lines in patients with rheumatoid arthritis and systemic lupus erythematosus. Annals of Allergy, 39(5):344-50.

Skurkovich et al. (1997) *Cytokine* 9(11): 899 (meeting abstract), entitled "The use of antibodies to cytokines (anti-IFN-α, anti-IFN-γ, anti-TNF-α) is an effective method for the treatment of rheumatic diseases-rheumatoid arthritis (RA), systemic lupus erythematosus (SLE), psoriatic arthritis (PA), and Behcet's syndrome (BS)."

Skurkovich et al. (2002) *Med. Hypotheses* 59(6): 770-80, entitled "Anticytokine therapy—new approach to the treatment of autoimmune and cytokine-disturbance diseases."

Staehelin et al. (1981) *Proc. Nat'l. Acad. Sci. USA* 78(3): 1848-52, entitled "Production of hybridomas secreting monoclonal antibodies to the human leukocyte interferons."

Stewart (2003) *Cytokine Growth Factor Rev.* 14(2): 139-54, entitled "Neutralizing interferon alpha as a therapeutic approach to autoimmune diseases."

Tsukui et al. (1986) *Microbiol. Immunol.* 30(11): 1129-39, entitled "A monoclonal antibody with broad reactivity to human interferon-alpha subtypes useful for purification of leukocyte-derived interferon."

Vancová et al. (2000) *J. Interferon Cytokine Res.* 20(5): 455-61, entitled "The carboxyterminal domains of human IFN-alpha2 and IFN-alpha8 are antigenically homologous."

Vilcek et al., (1986). In Aids: The epidemic of karposi's sarcoma and opportunistic infections. "The Role of Interferon in AIDS," A.E. Friedman-Klein & L.J. Laubenstein, eds. Masson Publishing, New York, New York, 193-198.

Viscomi et al. (1999) *J. Interferon Cytokine Res.* 19(4): 319-326, entitled "Antigenic characterization of recombinant, lymphoblastoid, and leukocyte IFN-alpha by monoclonal antibodies."

Zagury et al. (1999) *Biomed Pharmacother.* 53(2): 90-92, entitled "Anti-IFN alpha immunization raises the IFN alpha-neutralizing capacity of serum—an adjuvant to antiretroviral tritherapy."

Luft, T. et al., Type I IFNs enhance the terminal differentiation of dendritic cells, J. Immunol, vol. 161, No. 4, p. 1947-53 (1998).

Lyman, Stewart D., et al., "Plasma/serum Levels of flt3 Ligand Are Low in Normal Individuals and Highly Elevated in Patients with Fanconi Anemia and Acquired Aplastic Anemia", Blood, Dec. 1, 1995, pp. 4091-4096, vol. 86, No. 11.

McRea, Bradford, L., et al., "Interferon-α and -β inhibit the in vitro differentiation of immunocompetent human dendritic cells from $CD14^+$ precursors", Blood, Jul. 1, 2000, pp. 210-217, vol. 96, No. 1.

Pisarev, Vladimir M., et al., "Flt3 ligand enhances the immunogenicity of a *gag*-based HIV-1 vaccine", International Journal of Immunopharmacology, 2000, pp. 865-876, vol. 22.

Pfister, Otmar et al., "Chronic overexpression of membrane-bound flt3 ligand by T lymphocytes in severe aplastic anaemia", British Journal of Haematology, 2000, pp. 211-220, vol. 109.

Rabinovitch, Alex, "An Update on Cytokines in the Pathogenesis of Insulin-dependent Diabetes Mellitus", Diabetes/Metabolism Reviews, 1998, pp. 129-151, vol. 14.

Kawade and Watanabe, "The nature of neutralization reaction between effector protein and monoclonal antibody: a quantitative study of neutralization characteristics of anti-interferon antibodies", Immunology 56:489-495 (1985).

Kontsek et al., "Enhancement of neutralizing efficacy by combining three monoclonal antibodies to human interferon-alpha", Immunology, 73:8-11 (1991).

Mathian et al., "IFN-alpha induces lethal lupus in young, pre-autoimmune (New Zealand Black×New Zealand White) FE but not in BALB/c mice", J. Immunol., 174: 2499-2506 (2004).

Meager, A., "Natural autoantibodies to interferons", J. Interferon Cytokine Res., 17 Suppl. 1:S51-53 (1997).

Pascual et al., "The central role of dendritic cells and interferon-alpha in SLE", Curr. Opin. Rheumatol, 15:548-556 (2003).

Preble et al., "Systemic lupus erythematosus: presence in human serum of an unusual acid-labile leukocyte interferon", Science, 216:429-431 (1982).

Raanani et al., "Immune-medicated complications during interferon therapy in hematological patients", Acta Haematol, 107:133-144 (2002).

Shearer et al., "Monoclonal antibodies that distinguish between subspecies of human interferon-alpha and that detect interferon oligomers", J. Immunol., 133:3096-3101 (1984).

Weber et al. "Single amino acid changes that render human IFN-alpha 2 biologically active on mouse cells", EMBO J., 6:591-198 (1987).

Andriani, A., et al., "Autoimmune hemolytic anemia during alpha interferon treatment in nine patients with hematological diseases", Haematologica, May-Jun. 1996, pp. 258-260, vol. 81, No. 3, Abstract only.

Batocchi, A.P., et al., "Myasthenia gravis during interferon alfa therapy", Neurology, Feb. 1995, p. 382-383, vol. 45, No. 2, Abstract only.

Bohbot, N.L., et al. "Interferon-alpha-induced hyperthyroidism: a three-stage evolution from silent thyroiditis towards Graves, disease", Eur. J. Endocrinol., Mar. 2006, pp. 367-372, vol. 154, No. 3, Abstract only.

Brod, Staley A., "Ingested Type I Interferon: State of the Art as Treatment for Autoimmunity", Exp Biol Med, 2002, pp. 981-988, vol. 227.

Chieux, V., et al., "Increased levels of antiviral MxA protein in peripheral blood of patients with chronic disease of unknown etiology", J. Med. Virol., Oct. 2001, pp. 301-308, vol. 65, No. 2, Abstract only.

Landau, A., et al., "Acute autoimmune hemolytic anemia during interferon-alpha therapy for chronic hepatitis C", Dig. Dis. Sci., Jul. 1999, pp. 1366-1367, vol. 44, No. 7.

Murakami T., et al., "Prediction of interferon-alpha-induced thyroid dysfunction in patients with chronic hepatitis C.", J. Gastroenterol Hepatol., Sep.-Oct. 1995, p. 528-531, vol. 10, No. 5, Abstract only.

Oishi, A., et al., "Retinopathy is not the only ocular symptom: myasthenia gravis in association with interferon therapy", British Journal of Ophthalmology, 2005, pp. 1542-1543, vol. 89, Abstract only.

Rizzi, R., et al. "Autoimmune hemolytic anemia presenting during treatment of chronic hepatitis C with interferon alpha", Apr.-Jun. 2003, p. 107-110, vol. 18, No. 2, Abstract only.

Skurkovich, S. et al. "A Disturbance of Interferon Synthesis with the Hyperproduction of Unusual Kinds of Interferon can trigger Autoimmune Disease and Play a pathogenic Role in AIDS: The Removal of These Interferons can be Therapeutic", Medical Hypothesis, 1994, p. 27-35, vol. 42.

Stewart, T.A. et al. "Induction of type I diabetes by interferon-alpha in transgenic mice", Science, Jun. 25, 1993, p. 1942-1945, vol. 260, No. 5116.

Chuntharapai, A.; Lai, J.; Huang, X.; Gibbs, V.; Kim, K.J.; Presta, L.G.; Stewart, T.A. "Characterization and Humanization of Monoclonal Antibody That Neutralizes Human Leukocyte Interferon: a Candidate Therapeutic for IDDM and SLE" *Cytokine* vol. 15, No. 5, pp. 250-260 (Sep. 7, 2001).

Ehrenstein. M.R.; McSweeney, E.; Swane, M.; Worman, C.P.; Goldstone, A.H. "Appearance of Anti-DNA Antibodies in Patients Treated with Interferon-α" *Arthritis and Rheumatism* vol. 36, Issue 2, pp. 279-280 (Feb. 1993).

Fabris, P.; Bellerle, C.; Floreani, A.; Greggio, N.A.; de Lazzari, F. "Development of Type I Diabetes Mellitus Durhing Interferon Alpha Therapy for Chronic HCV Hepatitis" *Lancel* vol. 340, Issue 8818, p. 548 (Aug. 29, 1992).

Foulis, A.K.; Farquharson, M.A.; Meager, A. "Immuno-reactive α-Interferon in Insulin-Secreting β cells in Type I Diabetes Mellitus" *Lancet* vol. 2, Issue 8573, pp. 1423-1427 (Dec. 19, 1987).

Guerci, A.P.; Gueici, B.; Levy-Marchal, C.; Ongagna, J.; Ziegler, O. "Onset of Insulin-Dependent Diabetes Mellitus After Interferon-Alpha Therapy for Hairy Cell Leukemia" vol. 343, Issue 8906, pp. 1167-1168 (May 7, 1994).

Hooks, J.J.; Moulsopoulos, H.M.; Geis, S.A.; Slahl, N.I.; Decker, J.L. "Immune Interferon in the Circulation of Patients with Autoimmune Disease" *New England Journal of Medicine*; vol. 301, Issue 1, pp. 5-8 (Jul. 5, 1979).

Huang, X.; Yuang, J.; Goddard, A.; Foulis, A.; James, R.F.; Lemmark, A. "Interferon Expression in the Pancreases of Patients with Type 1 Diabetes" *Diabetes* vol. 44, Issue 6, pp. 658-664 (Jun. 1995).

Kim et al., Clin. Exp. Immunol., 70: 562-569 (1987).

Okanoue, T.; Sakamoto, S.; Itoh, Y.; Minami, M.; Yasui, K.; Sakamoto, M. "Side Effects of High-Dose Interferon Therapy for Chronic Hepatitis C" *Journal of Hepatology* vol. 25, Issue 3, pp. 283-291 (Sep. 1996).

Preble, O.T.; Rothko, K.; Klippel, J.H.; Friedman, R.M.; Johnston, M.I. "Interferon-Induced 2'-5' Adenylate Synthetase in Vivo and Interferon Production in Vitro by Lymphocytes from Systemic Lupus Erythematosus Patients With and Without Circulating Interferon" *Journal of Experimental Medicine* vol. 157, pp. 2140-2146 (Jun. 1983).

Ronnblum, L.E. et al. "Possible Induction of Systemic Lupus Erythemalosus by Interferon-α Treatment in a Patient With a Malignant Carcinoid Tumour" *Journal of Internal Medicine* vol. 227, Issue 3, pp. 207-210 (Mar. 1990).

Ronnblom, L.E.; Alm, G.V.; Orberg, K.E. "Autoimmunity After Alpha-Interferon Therapy for Malignant Carcinoid Tumors" *Annals of Internal Medicine*, vol. 115, Issue 3, pp. 178-183 (Aug. 1, 1991).

Schilling, P.J.; Kurzrock, R.; Kantarjian, H.; Gutteran, J.U.; Talpaz, M. "Development of Systemic Lupus Erythematosus After Interferon Therapy for Chronic Myelogenous Leukemia" *Cancer*, vol. 68, Issue 7, pp. 1536-1537 (Oct. 1, 1991).

Shiozawa, S.; Kuroki, Y.; Kim, M.; Hirohata, S.; Ogino, T. "Interferon-Alpha in Lupus Psychosis" *Arthritis and Rheumatism* vol. 35, Issue 4, pp. 417-422 (Apr. 1992).

Schmid, P.; Itin, P.; Cox, P .; McMaster, G.K.; Horisberger, M.A. "The Type I Interferon System is Locally Activated in Psoriatic Lesions" *Journal of Interferon Research* vol. 14, Issue 5, pp. 229-234 (Oct. 1994).

Spits, H.; Couwenberg, F.; Bakker, A.Q.; Weijer, K.; Uittenbogaart, C.H. "Id2 and Id3 Inhibit Development of CD34+ Stem Cells Into Predendritic Cell (Pre-DC)2 but Not Into Pre-DC1: Evidence for a Lymphoid Origin of Pre-DC-2" *Journal of Expreimental Medicine* vol. 192, Issue 12, pp. 1775-1783 (Dec. 18, 2000).

Vallin, H.; Perers, A.; Alm, G.V.; Ronnblom, L. "Anti-Double-Stranded DNA Antibodies and Immunoslimulatory Plasmid DNA in Combination Mimic the Endogenous IFN-α Inducer in Systemic Lupus Erythematosus" *Journal of Immunology* vol. 163, pp. 6306-6313 (1999).

von Wussow, P.; Jakschies, D.; Hochkeppel, H.; Horisberger, M. "MX Homologous Protein in Mononeuclear Cells from Patients with Systemic Lupus Erythematosus" *Arthritis and Rheumatism* vol. 32, Issue 7, pp. 914-918 (Jul. 1989).

Bennett et al., "Interferon and granulopoiesis signatures in systemic lupus erythematosus blood", J. Exp. Med., 197:711-723 (2003).

Blazar, Bruce, R., et al., "Flt3 Ligand (FL) Treatment of Murine Donors Does Not Modify Graft-Versus-Host Disease(GVHD) but FL Treatment of Recipients Post-Bone Marrow Transplantation Accelerates GVHD Lethality", Biology of Blood and Marrow Transplantation, vol. 7: 197-207, Apr. 2001.

* cited by examiner

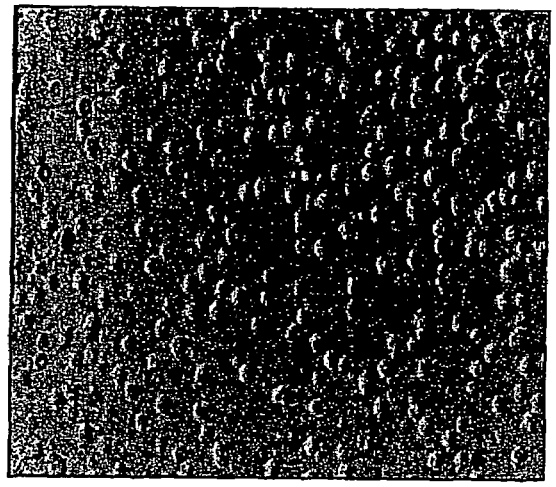
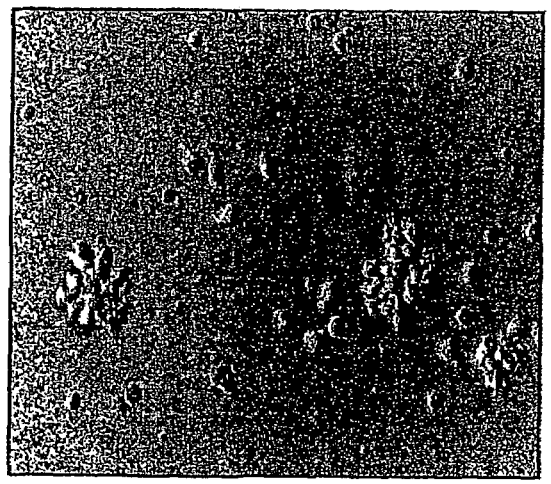
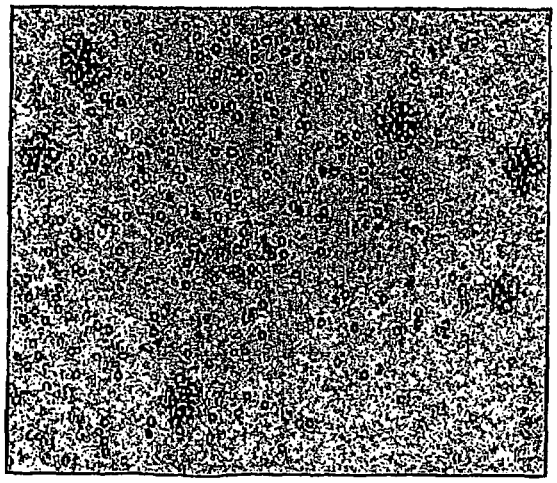

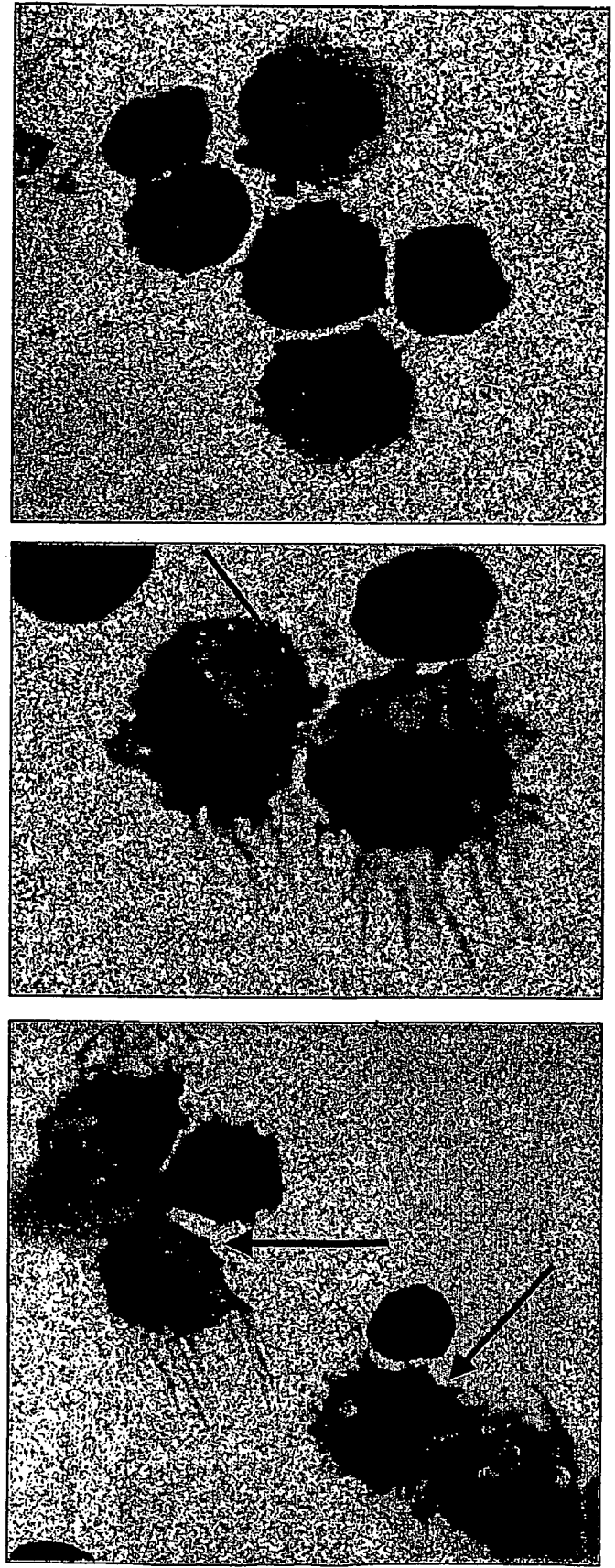

METHODS FOR TREATING AUTOIMMUNE DISEASES IN A SUBJECT AND IN VITRO DIAGNOSTIC ASSAYS

CROSS-REFERENCES TO RELATED APPLICATIONS

This application claims the priority to U.S. Provisional Patent Application Ser. No. 60/260,541, filed Jan. 9, 2001, the entire contents of which are hereby incorporated by reference.

FIELD OF THE INVENTION

This invention relates to treating autoimmune diseases and diagnostic assays related to autoimmune diseases.

BACKGROUND OF THE INVENTION

Autoimmune diseases are devastating and crippling diseases, and occur when a patient's own immune system turns against itself by attacking the patient's own body or tissues. One example of an autoimmune disease is systemic lupus erythematosus (SLE), which is characterized by multi-organ involvement and immunological abnormalities that include the presence of autoreactive T cells and B cells. Autoantibodies against the nucleosome appear to be a hallmark characteristic of SLE and suggest that inappropriate handling of dying (apoptotic) cells may represent a key pathogenic event in the development of SLE. SLE results from the dysregulation of both the humoral and the cellular limbs of the immune system indicating that the initial alteration may be at the level of cells that enroll and control the immune effectors, namely the dendritic cells (DCs).

Dendritic cells (DCs) are specialzed antigen presenting cells which elicit T cell mediated immune responses (Steinman, R. M. (1991) Ann. Rev. Immunology, Vol. 9, pp. 271-296 and Banchereau et al. (2000) Ann. Rev. Immunol. 18:767). DCs induce and sustain immune responses and have been shown to capture dying cells and present their antigens to $CD4^+$ T cells, which then activate other immune effectors including B cells. DC progenitors in the bone marrow give rise to circulating precursors that home to the tissue where they reside as immature cells with high phagocytic capacity. Upon tissue damage, DCs capture antigen (Ag) and subsequently migrate to the lymphoid organs where they select rare Ag-specific T cells, thereby initiating immune responses. DCs present antigen to CD4+ T cells which in turn regulate the immune effectors including antigen-specific ones such as CD8+ T cells and B cells as well as nonspecific ones such as macrophages, eosinophils and NK cells. DCs can also directly activate B cells and induce their differentiation into plasma cells in vitro.

Three subsets of DC precursors ("DCpre") circulate in the blood: (1) $CD14^+$ monocytes, (2) $CD11c^+$ myeloid DCpre and (3) $CD11c^-$ plasmacytoid (lymphoid) DCpre. Monocytes can differentiate into cells displaying features of immature DCs or macrophages (MΦ). The immature DCs become mature DCs upon treatment with CD40L and/or LPS or when cultured with a combination of cytokines including TNF, IL-1 and IL-6. $CD11c^+$ myeloid DCpre give rise to interstitial DC (intDC), Langerhans cells (LC) or MΦ depending on local cytokine environment.

$CD11c^-$ IL-3R$\alpha^+$ lymphoid DC precursors are a major source of interferon-alpha (IFN-α). High levels of IFN-α are often found in lupus serum (Kim et al., Clin. Exp. Immunol. 70:562-269, 1987). Furthermore, IFN-α treatment often induces the appearance of autoantiodies and eventually the development of autoimmune diseases including SLE (Ronnblum et al., J. Intern. Med. 227:207-210, 1990). Anti-IFN-α antibody has been reported in SLE patients (Suit et al., Clin. Exp. Rheumatol. 1:133-135).

Plasmacytoid DCs have been reported to produce IFN-α which in turn affects differentiation of myeloid DCs and growth and activation of B cells. Spits et al. (J Exp Med 192(12):1775-84, 2000) and Blom et al. (J Exp Med 192(12): 1785-96. 2000) report that $CD11c^-$ plasmacytoid DCs are of lymphoid origin in humans. Siegal et al. (Science 284:1835, 1999) report that lymphoid DCs (plasmacytoid DCs) produce large amounts of IFN-α when exposed to inactivated herpes simplex virus. Cella et al., (Nature Medicine 5(8):868-70, 1999) report that lymphoid DCs (plasmacytoid DCs) produce large amounts of IFN-α in response to influenza virus as well as CD40 ligation.

The autoantibodies (autoAbs) in SLE can be characterized in three major categories: (1) anti-nuclear and anti-double stranded DNA antibodies; (2) autoAbs directed against the surface of endothelial cells and platelets (anti-phospholipids/ 12 glycoprotein); and (3) autoAbs directed against molecules on the surface of hematopoietic cells (see, e.g., review of Cabral and Alarcon-Segovia (1998) Curr. Opin. Rheumatol. 10:409). In addition to the direct damage caused by cellular and/or tissue antigen-antibody interactions, many of the disease's symptoms result from indirect damage through the deposition of immune complexes on tissues. This mechanism has been shown to be responsible for some forms of SLE nephritis, arthritis, and vasculitis (Laihta, R. G. 1999. Systemic Lupus Brythematosus. Academic Press; Kammer, G. M., and G. C. Tsokos. 1999. Lupus, Humana Press). Defects in immune complex clearance, including include Fc receptor ("FcR") and C3b-receptor ("C3b-R") dysfunction, as well as genetic defects in complement proteins and C-reactive protein (all of which are essential players in the removal of anti-DNA/nucleosome complexes) can contribute to the development of SLE (Lahita, R. G. 1999. Academic Press; Kammer, G. M., and G. C. Tsokos. 1999 Humana Press). B cells play a major role in SLE pathogenesis, as they are responsible for the production of autoantibodies and hypergammaglobulinemia.

Hooks et al. (N. Engl. J. Med. 301:5, 1979) describe the presence of circulating immune interferon in patients with autoimmune disease including SLE. Kim et al. disclosed that the levels of IFN-α correlated with the clinical activity index. Preble et al. (J. Exp. Med. 157:214, 1983) and von Wussow et al. (Arthritis Rheum. 32:914, 1989) disclose that high levels of 2-5A synthetase and MX protein, two proteins specifically induced by IFN-α, are found in the mononuclear cells of both serum IFN-positive and serum IFN-negative SLE patients. Vallin et al. (J. Immunol. 163:6306 1999) disclose that the IFN-α inducing factor acts on leukocytes with features of immature DCs. Batteux et al. (Eur. Cytokine Netw. 10:509, 1999) disclose that the induction of IFN-α production by SLE serum is dependent on FcγRII (CD32).

One complication of IFN-α therapy is the induction of autoimmune disorders (in about 4% to 19% of the cases), the most common being thyroid dysfunction (Bhrenstein et al., Arthritis Rheum. 36:279, 1993; Okanoue et al., J. Hepatol. 25:283, 1996; Ronnblom et al., Ann. Intern. Med. 115:178, 1991; Kalkner et al., Qjm. 91:393, 1998). Indeed, Schilling et al. (Cancer 68:1536, 1991) disclose that IFN-α a therapy can also induce SLE with a frequency of 0.15% to 0.7%. Every case is associated with the induction or marked increase in titers of antinuclear antibodies and anti-DNA antibodies.

Type I diabetes is another autoimmune disease in which IFN-α plays an important etiopathogenic role. Foulis et al. (*Lancet* 2:1423, 1987) and Huang et al. (*Diabetes* 44:658, 1995) disclose a strong correlation between the expression of IFN-α by the pancreatic islets and the development of autoimmune diabetes in humans. Furthermore, Chakrabarti et al. (*J. Immunol.* 157:522, 1996) disclose that expression of IFN-α by B cells within pancreas Langerhans islets causes diabetes in a transgenic mouse model. Additionally, Fabris et al. (*Lancet* 340:548, 1992) and Guerci et al. (*Lancet* 343: 1167, 1994) disclose that IFN-α therapy can induce Type I diabetes in humans.

FMS-like tyrosine kinase 3 ("Flt3") is a member of the type III tyrosine kinase receptor family which also includes KIT (c-kit RTK), FMS (M-CSF RTK) and platelet-derived growth factor (PDGF) receptor. Similar to the ligands for the KIT and FMS receptors, stem cell factor and M-CSF, respectively, the Flt3 receptor is activated by a cognate molecule, termed Flt3-ligand ("Flt3L"). Flt3 is a variant form of a tyrosine kinase receptor that is related to the c-fms and c-kit receptors (Rosnet et al. *Oncogene*, 6,1641-1650, 1991). Flt3L is a hematopoietic cytokine that has been shown to facilitate the expansion of DCs and the generation of antitumor immune responses (see U.S. Pat. No. 5,554,512, "Ligands for Flt3 Receptors"). Flt3L has been found to regulate the growth and differentiation of progenitor and stem cells (Blazar et al. (2001) *Biology of Blood and Marrow Transplantation* 7:197-207 and see U.S. Pat. No. 5,843,423). Flt3L treatment of monocyte cell cultures was shown to result in a marked expansion in the absolute number of myeloid- and lymphoid-related DCs and a reduction in the proportion of donor splenic T cells (Blazar et al).

All of the disclosures of the publications which are referred to within this application (including U.S. patents, published PCT applications, scientific references, books, manuals, etc.) are hereby incorporated by reference in their entireties into this application.

SUMMARY OF THE INVENTION

The present invention is directed to methods for treating an autoimmune disease in a subject which comprises administering to the subject an effective amount of (a) at least one interferon antagonist that reduces activity of a type I interferon, and (b) at least one Flt3 ligand (Flt3L) antagonist that reduces activity of Flt3L, to thereby reduce differentiation of monocytes into dendritic cells in the subject and treat the autoimmune disease.

The invention is also directed to a therapeutic composition to inhibit monocyte differentiation into dendritic cells capable of antigen presentation which comprises (a) at least one interferon antagonist that reduces activity of a type I interferon, and (b) at least one Flt3 ligand (Flt3L) antagonist that reduces activity of Flt3L. Such compositions constitute therapeutic compositions for the treatment of autoimmune diseases including, but not limited to, SLE and other IFN-α mediated autoimmune diseases including but not limited to diabetes, arthritis, AIDS, psoriasis and thyroiditis.

The invention is also directed to an in vitro assay for determining a subject's risk for developing an autoimmune disease which comprises (a) obtaining a serum sample from the subject; (b) quantifying IFN-α and Flt3 ligand (Flt3L) in the serum sample; and (c) comparing the quantity of IFN-α and Flt3L with the quantities of IFN-α and Flt3L in serum from subjects with an autoimmune disease, thereby determining the subject's risk for developing an autoimmune disease.

The invention is also directed to a kit for determining a subject's risk for developing an autoimmune disease or for monitoring the status of an autoimmune disease in a subject which comprises an amount of a composition which specifically binds to Flt3L and to IFN-α effective to detect Flt3L and IFN-α in a biological sample of a subject. The kit contains a composition comprising (a) a monoclonal antibody that binds Flt3L and (b) a monoclonal antibody that binds IFN-α. Further, the composition is detectable. The kit can include one or more reagents for detecting amounts of the composition bound to one or more samples.

BRIEF DESCRIPTION OF THE DRAWINGS

FIGS. 2A-2E are photographic illustrations showing purified monocytes from normal donors which cluster and acquire dendritic cell morphology when cultured with serum from patients with SLE but not when cultured with autologous (AS) serum Monocytes are cultured with AS serum (FIG. 2C) or SLE serum (FIGS. 2A-2B). FIG. 2D depicts a cluster of veiled cells induced by SLE sera. In FIG. 2E, Giemsa staining of cytospun monocytes cultured for 24 hours with SLE serum reveals cells with morphology typical of mature DCs. ("SLE-DCs"=SLE serum induced DCs).

FIGS. 7A, 7B and 7C are photographic illustrations which depict capture of autologous apoptotic cells by SLE-DCs. Giemsa stained cytospins of overnight monocyte cultures with SLE serum (FIGS. 7A and 7B) and AS serum (FIG. 7C). Arrows indicate the capture of cell fragments in cultures with SLE serum.

FIG. 8A depicts flow cytometry results showing SLE-DCs capture DNA containing apoptotic bodies as indicated by an increase in 7AAD levels. Loaded DCs are used as stimulators of autologous CD4+ T cell proliferation (measured by thymidine incorporation, vertical axis) (FIG. 8B).

FIG. 9A shows the correlation between inducing activity and SLEDAI. FIG. 9B shows the correlation between inducing capacity and IFN-α levels in serum. Each point on each graph represents serum taken from a patient.

FIG. 13A shows relative BAFF expression (ng/ng 18S ribosomal RNA) in monocytes cultured for 72 hours under indicated conditions (IFN-α U/mL). NI denotes control uncultured monocytes from the same donor. FIG. 13B shows relative BCMA expression (ng/ng18S) in PBMC, uncultured (NI) or cultured with 1000 U/mL IFN-α for indicated number of hours. Relative RNA expression was assessed by real time PCR using the ABI PRISM 7700 Sequence Detection System (ABI). The ratio of the target expression (BAFF or BCMA) against a reference (18S ribosomal RNA) gives normalized expression levels.

FIG. 14A shows that neutralization of endogenous TNF results in sustained IFN-α release by CD123+ pDC. The vertical axis shows levels of IFN-α in ng/mL of culture supernatant generated under the indicated conditions. FIGS. 14B-14C show that adding TNF to pDCs inhibits virus-induced IFN-α release. FIG. 14B shows on the vertical axis the percentage of inhibition of IFN-α secreted into the culture supernatant. FIG. 14C shows on the vertical axis levels of IFN-α in ng/mL of culture supernatant.

DETAILED DESCRIPTION

Figure 1:
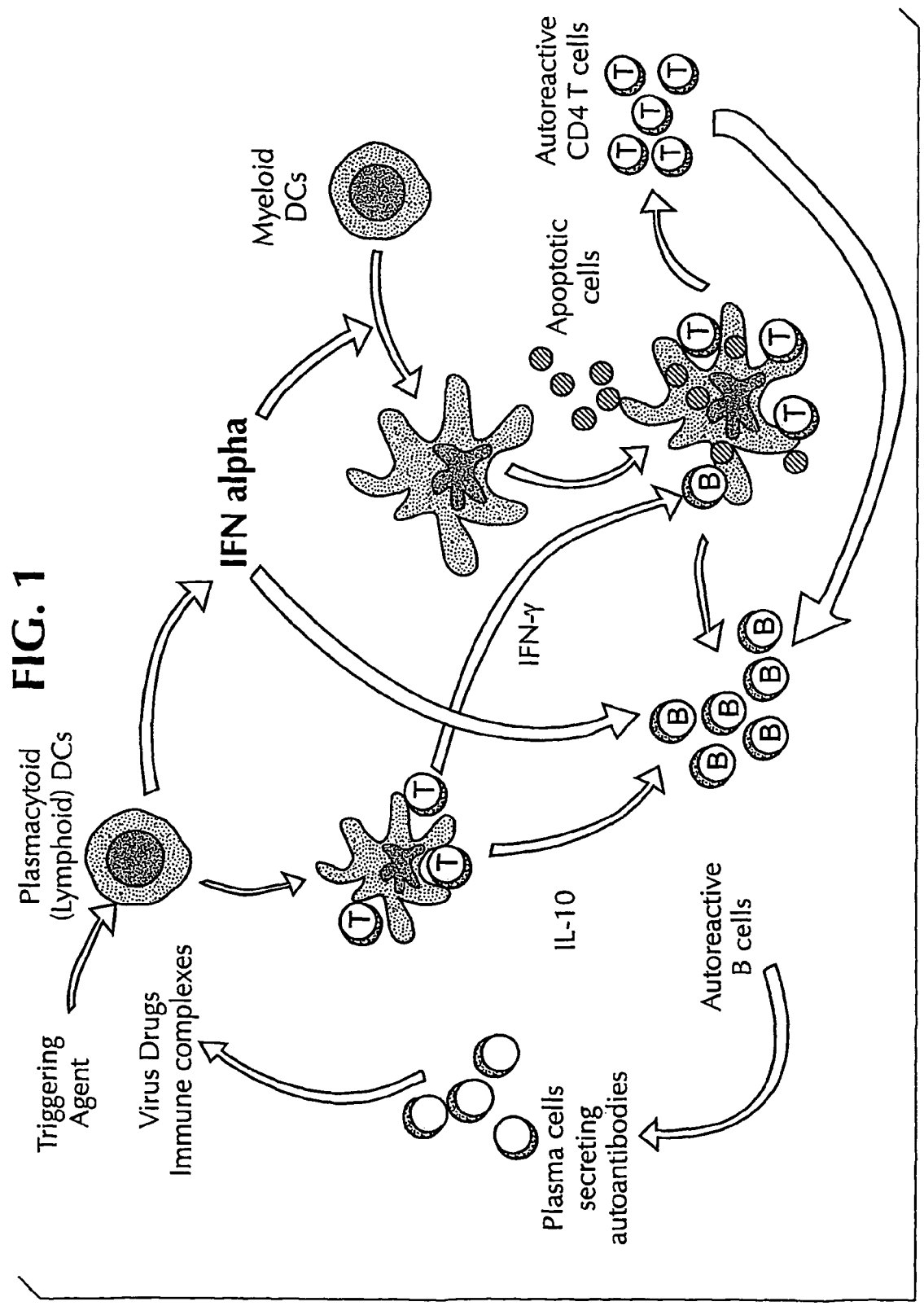
FIG. 1 is a schematic representation of interactions between dendritic cell subsets in SLE which shows the relationship between lymphoid (plasmacytoid) DCs and/or their products, e.g., type I interferons, and the differentiation of myeloid DCs. The differentiation of myeloid DCs initiate the cascade of antigen presentation that leads to differentiation of autoreactive T cells and B cells contributing to SLE pathogenesis.

The present invention is directed to methods for treating an autoimmune disease in a subject which comprises administering to the subject an effective amount of (a) one or more interferon antagonists that reduce activity of a type I interferon, and (b) one or more Flt3 ligand (Flt3L) antagonists that reduce activity of a Flt3L, to thereby reduce differentiation of monocytes into dendritic cells in the subject and treat the autoimmune disease. Additionally, the present invention provides a composition useful for inhibiting monocyte differentiation into dendritic cells (DCs) which are capable of antigen presentation, which comprises: (a) at least one interferon antagonist that reduces activity of interferon, and (b) at least one Flt3 ligand antagonist that reduces activity of a Flt3 ligand. For example, one component of the composition can be an antagonist that reduces or inhibits the binding or interaction between the type I interferon (e.g., IFN-α) and its receptor. This composition also includes an antagonist that reduces or inhibits binding or interaction between a Flt3L and its receptor.

As used herein, "SLE-DCs" refers to dendritic cells which are obtained by culturing monocytes with serum obtained from a patient with SLE ("SLE serum").

As used herein, an "interferon antagonist" encompasses a antibody, an antigen-binding fragment of an antibody, a polypeptide, a peptidomimetic, a nucleic acid encoding a polypeptide, an organic molecule or any combination thereof which is capable of reducing the activity or function of a type I interferon in a cell within a subject or a cell in vitro.

As used herein, "polypeptide" encompasses peptides and proteins of any length, without regard to function.

As used herein, a "type I interferon" includes IFN-α, IFN-β, IFN-varpi and IFN-tau. Oritani et al. ((2001) *Cytokine Growth Factor Rev.* 12(4):33748) provide a description of other examples of a type I interferon.

Interferon antagonists interfere with the interaction between a type I interferon (such as IFN-α) and its receptor which results in a reduction in the generation of antigen-presenting cells by reducing differentiation of monocytes into DCs which become antigen presenting cells. The reduction in generation of antigen-presenting cells can be achieved by one or more different mechanisms, but the exact mechanism by which this occurs is not crucial to the invention. For example, TNF and/or agonistic anti-TNF receptor antibodies can reduce type I interferon secretion by accelerating the differentiation of pDCs into type I IFN non-producing cells.

There are numerous assays which can be performed to identify whether a compound is an interferon antagonist useful in the present invention. These assays are known to those of skill in the art. One assay is a dendritic cell differentiation assay where a compound to be tested is added to a culture of monocytes under conditions suitable for monocyte differentiation into DCs. The conditions include the addition of either SLE serum or interferon so that the monocytes are induced to differentiate into DCs. Thus, if the compound causes an inhibition of interferon and/or SLE serum driven monocyte differentiation into DCs as compared to differentiation of monocytes in cultures which do not have the compound added, then the compound is an interferon antagonist.

Another assay to identify compounds which are interferon antagonists is a binding assay wherein inhibition of binding of labeled interferon to a receptor on a cell is measured. If a compound is able to inhibit the binding of interferon to its receptor or to cells having interferon receptors, the compound is an interferon antagonist.

In addition, an assay to determine whether a compound is an interferon antagonist is an assay to measure inhibition of interferon produced by cells in response to triggers that normally induce interferon production and/or secretion, for instance viruses. Thus, if in the presence of the compound and the trigger (e.g., a virus), a cell which would normally produce interferon does not produce interferon, or produces interferon at a reduced level, then the compound is an interferon inhibitor.

Another assay to determine whether a compound is an interferon antagonist is a tumor cell survival assay. Interferon has anti-tumor activity by direct growth inhibition and/or induction of tumor cell death. The examples of such tumor cells susceptible to interferon include melanoma cell lines. This tumor cell survival assay measures the survival of otherwise susceptible melanoma cells which are cultured in the presence of interferon and an interferon antagonist. Therefore, if the tumor cells are surviving in the culture containing the compound to be tested as compared to an identical culture which does not have the compound to be tested, then the compound is an interferon antagonist.

Another assay to identify whether a compound is an interferon antagonist is an assay to quantify expression (at the protein and/or RNA level) of interferon-inducible proteins including MXA protein, and interferon regulatory factors, as examples. Therefore, a compound to be tested is added to the culture and protein and RNA levels of the specified interferon-inducible proteins are measured. If the addition of the compound decreases the levels of the protein and/or mRNA expression, then the compound is an interferon antagonist.

Another assay to determine whether a compound is an interferon antagonist is an in vitro protective assay. Normally, adding interferon to a cell culture protects the cells from cytolytic activity of a virus which is introduced into the cell culture, thus increasing cell survival in the culture. Thus, adding an interferon antagonist abolishes protection and cell survival will not be increased. Therefore, if inhibition of antiviral activity of interferon is measured, then the compound is an interferon antagonist. The inhibition measurement is based on the determination of death of cells susceptible to virus.

An example of an interferon antagonist includes, but is not limited to, a monoclonal antibody that specifically binds IFN-α. Another example of an interferon antagonist is a soluble IFN-α receptor. The soluble receptor is useful to bind to circulating type I interferon and thus prohibit it from binding with its natural receptor and causing progression of monocyte differentiation into DCs. In another embodiment of the invention, the interferon antagonist can be an organic molecule which binds to the IFN-α receptor, but does not cause downstream effects of such binding, I.e., an non-functional receptor ligand mimic. Such an organic molecule can specifically bind to the IFN-α binding pocket of the receptor without causing receptor activation, so as to displace any IFN-α which could so bind and thereby render the receptor ineffectual In a further embodiment of the invention, the interferon antagonist includes a peptide which comprises the complementarity determining region (CDR) of the monoclonal antibody which specifically binds interferon or Flt3L or both. In yet another embodiment of the invention, the interferon antagonist is a fusion peptide.

Interferon antagonists useful in the present invention can reduce the activity of the type I interferon by many different mechanisms and the invention is not dependent on any particular mechanism. An interferon antagonist of the present invention includes but is not limited to, a modified IFN-α which has reduced or no activity in vivo. With regard to disrupting the generation of antigen-presenting cells by type I interferon, the interferon antagonist can affect the activity of type I interferon at many different junctions in the signaling pathway of interferon. As some examples, the antagonist can block activity of the interferon protein itself; block activity of the type I interferon receptor; inhibit binding of the interferon to the receptor; block type I interferon signaling and/or transduction pathways; block type I interferon release from cells which normally produce it; block generation of cells which normally make type I interferon; and block secretion of type I interferon from cells which normally secret it. The inhibition of the differentiation or generation of cells which normally produce interferon can result from administration of TNF and/or agonistic anti-TNF receptor(s) antibodies and/or molecules providing TNF-like signaling to cells. These types of compounds are examples of interferon antagonists provided by the present invention. In addition, inactivation of type I interferon co-factors needed for the differentiation and growth of antigen presenting cells is another possible mechanism of an interferon antagonist of the invention.

As used herein, an "Flt3L antagonist" encompasses an antibody, an antigen-binding fragment of an antibody, a polypeptide, a peptidomimetic, a nucleic acid encoding a polypeptide, an organic molecule or any combination thereof which is capable of reducing the activity of Flt3L. For example, the Flt3L antagonist can interfere with the interaction between Flt3 ligand ("Flt3L") and its receptor so as to inhibit differentiation of progenitor cells into dendritic cells. The reduction in generation of antigen-presenting cells can be achieved by one or more different mechanisms. For example, Flt3L can contribute to unabated DC activation that can in turn drive auto-antigen presentation in SLE, therefore, Flt3L is a target for therapeutic intervention. Flt3L likely plays a role in the development or the sustainment of the SLE autoimmune disease making an antagonist of Flt3L function useful for the treatment of autoimmune diseases.

In one embodiment, an assay to identify a therapeutically effective amount of an interferon antagonist is to determine the amount of interferon antagonist necessary to reduce interferon receptor binding in vitro to serum taken from a subject to be treated. In this example, the concentration necessary to reduce binding by 50% in vitro will be effective therapeutically in vivo. A similar assay for Flt3L can be carried out to determine the effective amount of Flt3L antagonist for a particular subject or patient.

There are numerous assays which can be performed to identify whether a compound is a Flt3L antagonist useful in the present invention. One assay is a dendritic cell differentiation assay where a compound to be tested is added to a culture of monocytes under conditions suitable for monocyte differentiation into DCs. The conditions include the addition of Flt3L to the monocyte culture so that the monocytes are induced to differentiate into DCs. Thus, if the compound causes at least a 50% inhibition of monocyte differentiation into DC as compared to cultures of monocytes which do not have the compound added, the compound is a Flt3L antagonist.

Another assay to determine whether a compound is a Flt3L antagonist is an assay to determine inhibition of binding of labeled Flt3L to its receptor. In this assay, a detectable label is attached to Flt3L and the labeled Flt3L is permitted to bind to its receptor in the presence and in the absence of the compound. If the presence of the compound causes a decrease in the binding of the Flt3L to the receptor, than the compound is a Flt3L antagonist.

Another assay useful to determine whether a compound is a Flt3L antagonist is an in vitro proliferation assay. Human hematopoietic progenitor cells are cultured with Flt3L in order to induce their differentiation and/or proliferation. The compound to be tested is added to some cultures and others are compound-free. A comparison is made between the cultures with the compound and those without to determine the amount of proliferation and differentiation. If there is inhibition of Flt3L driven proliferation and/or differentiation of human hematopoietic progenitor cells, then the compound is a Flt3L antagonist.

Another assay useful to determine whether a compound is a Flt3L antagonist is an in vitro proliferation assay. Human factor-dependent B cell lines are cultured with and without the compound added to the culture. An example of such a cell line is a cell line engineered to express Flt3. If the cultures with the compound added show at least 50% inhibition of Flt3L driven proliferation of human factor-dependent B cell lines, then the compound is a Flt3L antagonist.

Another assay useful to determine whether a compound to be tested is a Flt3L antagonist is an in vivo assay. Mice are administered Flt3L and their hematopoietic cells, including dendritic cells are expanded in vivo. These mice are either administered the compound to be tested, or not and the levels of hematopoietic cells in the mice are measured. Thus, inhibition of Flt3L-mediated expansion of hematopoietic cells, including dendritic cells, in vivo in mice indicates that the compound is a Flt3L antagonist.

One example of a Flt3L antagonist is a monoclonal antibody which specifically binds Flt3L. Another example of a Flt3L antagonist is a soluble Flt3L receptor. The soluble receptor is useful to bind circulating Flt3L to prohibit Flt3L from binding with its natural receptor and causing progression of monocyte differentiation into DCs. In one embodiment of the invention, the Flt3L antagonist can be an organic molecule which binds to the Flt3L receptor, but does not cause down-stream effects of such binding, i.e., a receptor ligand mimic. Such an organic molecule can specifically bind to the Flt3L binding pocket of the receptor to displace any Flt3L which would otherwise so bind. The Flt3L antagonist of the invention also includes a polypeptide which comprises the complementarity determining region (CDR) of the above-mentioned monoclonal antibody, or fusion peptides therewith.

The term "human monoclonal antibody" (HuMAb) as used herein, means HuMAbs obtainable from human B cells (e.g., whether the antibody is prepared by culturing the immortalized and/or activated human B cells or recombinantly from human B cell cDNAs encoding such a HuMAb and whether or not the antibody is bound to a molecule which can alter its biological activity, e.g., a receptor or ligand, an enzyme, a toxin, a carrier, etc.) and antibodies that are made by recombining the variable portions of a HuMAb of the present invention of one isotype (e.g., an $IgG_4$) with the constant region of a human antibody of another isotype (e.g., a human $IgG_1$, $IgG_2$, $IgG_3$, $IgG_4$, IgA, IgD, IgM or IgE). Recombinant methods for making these HuMAbs are known in the art (see U.S. Pat. No. 5,959,085).

The use of a combination of an interferon antagonist and a Flt3L antagonist may achieve the advantage of using much less of each molecule to reduce generation of DCs. Such synergy is advantageous in allowing reduction of the therapeutically effective amounts of each antagonist in the methods and compositions of the invention.

In one embodiment of the invention, either the interferon antagonist or the Flt3L antagonist or both can be a polypeptide. The polypeptide may be a peptidomimetic, a synthetic polypeptide, a derivative of a natural polypeptide, a modified polypeptide, a labeled polypeptide, or a polypeptide which includes non-natural peptides. The polypeptide may be wholly or partially a non-natural polypeptide which has chirality not found in nature, i.e. D-amino acids or L-amino acids. The use of a non-natural linkage in such a peptide can prolong half-life and protect the peptide from degradation by naturally occurring enzymes.

In another embodiment of the invention, the autoimmune disease is selected from the group consisting of acquired immune deficiency syndrome (AIDS), ankylosing spondylitis, arthritis, aplastic anemia, Behcet's disease, diabetes, graft-versus-host disease, Graves' disease, hemolytic anemia, hypogammaglobulinemia, hyper IgE syndrome, idiopathic thrombocytopenia purpura (ITP), multiple sclerosis (MS), Myasthenia gravis, psoriasis, lupus and any combination thereof.

The diabetes can be, but is not limited to, diabetes mellitus, Type I diabetes, Type II diabetes, juvenile on-set diabetes or any combination thereof. The arthritis can be, but is not limited to, rheumatoid arthritis, juvenile rheumatoid arthritis, psoriatic arthritis or any combination thereof. The lupus can be systemic lupus erythematosus (SLE) or drug-induced lupus.

In one embodiment of the invention, the subject is a mammal. The mammal can be a human or a primate. The subject can be a human patient, or an animal which exhibits symptoms of a human immune disease and is therefore an animal model of a human disease, such as a murine transgenic disease model or a primate disease model or a model of human disease established in a SCID mouse reconstituted with the human immune system. The mammal can be, but is not limited to, a human, a primate, a rat, a dog, a cat, a swine. In another aspect of the invention, the subject is a murine subject, a bovine subject, a primate subject, an equine subject, a swine subject, or a canine subject. The subject, in another aspect of the invention, suffers from SLE.

In one embodiment of the invention, the interferon antagonist comprises an anti-IFN-α antibody or an antigen-binding fragment thereof. In another embodiment of the invention, the interferon antagonist is TNF. In yet another embodiment of the invention, the Flt3L antagonist comprises an anti-Flt3L antibody or an antigen-binding fragment thereof.

In an embodiment of the invention, the antibody which can be an element of the composition comprises a monoclonal antibody, a chimeric antibody, an anti-idiotypic antibody, a humanized antibody, a primatized antibody and any combination thereof.

In another embodiment of the invention, the interferon antagonist and the Flt3L antagonist are part of one molecule. In one embodiment of the invention, the effective amount of the interferon antagonist is in a range of about 1 to about 10 fold molar excess over the amount of interferon in the subject's serum. In another aspect of the invention, the effective amount of the Flt3L antagonist is in a range of about 1 to about 10 fold molar excess over the amount of Flt3L in the subject's serum.

The method of the invention includes administering a composition to a subject wherein the composition inhibits induction by IFN-α of myeloid DC maturation into DCs which have antigen-presenting activities. The administration of the composition can be intraveneous, via a subdural injection, oral topical, cutaneous, subcutaneous, parenteral or by aerosol. The administration of the composition of the invention to a subject encompasses intralesional intraperitoneal, intramuscular or intravenous injection; infusion; liposome-mediated delivery, or topical, nasal, oral ocular or otic delivery. In a further embodiment, the administration includes intrabronchial administration, anal or intrathecal administration. The composition of the invention may be delivered hourly, daily, weekly, monthly, yearly (e.g. in a time release form) or as a one time delivery. The delivery may be continuous delivery for a period of time, e.g. intravenous delivery. The preferred route and timing of delivery can be readily determined by those of skill in the art.

In one embodiment of the invention, the interferon antagonist reduces binding of a type I interferon with its receptor. In another embodiment, the interferon antagonist interferes with signal transduction following interferon binding to receptor on cells in the subject. In another embodiment, the interferon antagonist reduces production of interferon by cells in the subject. In another embodiment, the interferon antagonist reduces interferon secretion by cells in the subject. In yet another embodiment, the interferon antagonist reduces bioavailability of interferon in the subject. In a further embodiment, the interferon antagonist is TNF.

In another embodiment of the invention, the composition further comprises a carrier. In another embodiment of the invention, the carrier comprises an aqueous carrier, a liposome, or a lipid carrier.

The compounds which comprise the composition of the present invention can be a peptidomimetic compound(s) which can be at least partially unnatural. The peptidomimetic compound can be a small molecule mimic of a portion of the amino acid sequence of Flt3L or of Flt3L receptor or a type I interferon or a type I interferon receptor. The compound can have increased stability, efficacy, potency and bioavailability by virtue of the mimic. Further, the compound can have decreased toxicity. The peptidomimetic compound can have enhanced mucosal intestinal permeability. The compound may be synthetically prepared. The compound of the present invention can include L-, D- or unnatural amino acids, α,α-disubstituted amino acids, N-alkyl amino acids, lactic acid (an isoelectronic analog of alanine). The peptide backbone of the compound may have at least one bond replaced with PSI-[CH=CH]. The compound can further include trifluorotyrosine, p-Cl-phenylalanine, p-Br-phenylalanine, poly-L-propargylglycine, poly-D,L-allylglycine, or poly-L-allylglycine.

One embodiment of the present invention is a peptidomimetic compound wherein the compound has a bond, a peptide backbone or an amino acid component replaced with a suitable mimic. Examples of unnatural amino acids which may be suitable amino acid mimics include β-alanine, L-α-amino butyric acid, L-γ-amino butyric acid, L-α-amino isobutyric acid, L-ε-amino caproic acid, 7-amino heptanoic acid, L-aspartic acid, L-glutamic acid, cysteine (acetamindomethyl), N-ε-Boc-N-α-CBZ-L-lysine, N-ε-Boc-N-α-Fmoc-L-lysine, L-methionine sulfone, L-norleucine, L-norvaline, N-α-Boc-N-δCBZ-L-ornithine, N-δ-Boc-N-α-CBZL-ornithine, Boc-p-nitro-phenylalanine, Boc-hydroxyproline, Boc-L-thioproline.

In one embodiment, the compound is a peptide wherein the free amino groups have been inactivated by derivitization. For example, the peptide can be an aryl derivative, an alkyl derivative or an anhydride derivative. The peptide can be acetylated. The peptide is derivatized so as to neutralize its net charge.

One embodiment of the composition of the invention is a ribozyme which is capable of cleaving mRNA coding for either the type I interferon or the Flt3L. See Cech, et al., U.S. Pat. No. 4,987,071; Altman et al., U.S. Pat. No. 5,168,053; Haseloff et al, U.S. Pat. No. 5,254,678 published European application No. Hampel et al., EP 360,257. The therapeutic composition of the invention, in one embodiment, is a ribozyme that is recombinant and that has been engineered to cleave type I interferon mRNA and/or Flt3L mRNA. In another aspect of this invention, the composition can comprise a recombined nucleic acid which is a ribozyme capable of cleaving both the mRNA coding for IFN-α and the mRNA coding for Flt3L. In addition, the invention provides for an antisense nucleic acid which is capable of binding to the mRNA coding for either the Flt3L or the type I interferon and inhibiting translation of such mRNA into protein.

The invention provides that dendritic cells are key factors in the etiopathogenesis of SLE and other autoimmune diseases, and as such, dendritic cells and/or their products are key targets for therapy of SLE and other autoimmune diseases. As an example of an autoimmune disease, SLE is a disease wherein lymphoid DCs release large amounts of cytokines, including IFN-α which subsequently activate myeloid DCs to trigger and sustain autoimmune reactions. This interaction between DC subsets provides an explanation for the (1) profound B cell alterations with a broad spectrum of autoantibodies, mainly against nuclear antigens, (2) autoreactive CD4+ T cells and (3) high levels of type I interferon found in serum from patients with SLE. These observations support the significant involvement of dendritic cells in the etiopathogenesis of SLE and other autoimmune diseases.

FIG. 1 illustrates the consequences of uncontrolled IFN-α release and its role in SLE pathogenesis as disclosed herein. The SLE initiating injury is an element that triggers plasmacytoid (lymphoid) DCs to secrete IFN-α in an uncontrolled manner. The triggering elements include viruses, bacteria, fungi and their products such as CpG DNA as well as drugs. The uncontrolled IFN-α release originates with a permanent plasmacytoid (lymphoid) DC activator such as chronic viral infection, or with an immune complex that is not cleared properly from the circulation, e.g. through FcR polymorphism or absence of complement components). The plasmacytoid DCs differentiate into mature DCs able to present the triggering element to T cells. The released IFN-α (possibly with other cytokines) induces the activation of circulating precursors of myeloid DCs, including monocytes, that capture apoptotic cells present in increased amounts in SLE blood. The myeloid DCs process the apoptotic cells and present their antigens to autoreactive T cells and/or to B cells. The autoreactive T cells, together with the DCs loaded with apoptotic cells now further activate the autoreactive B cells. These differentiate into plasma cells with help from the DCs. IFN-α also directly contributes to the generation of autoreactive B cells because it can turn on a partial germinal center phenotype (induction of CD38) characteristic of the circulating blood B cells in SLE.

Using monocytes, the most abundant precursors of myeloid DCs, from blood of healthy donors, a method has been developed for inducing immunogenic DC using serum from patients with SLE. Such DCs are active antigen presenting cells that can capture apoptotic cells and present their antigens to autologous CD4+ T cells, thus driving their activation and proliferation. Such sequence of events explain the pathogenic events in SLE. Formation of such DCs can be prevented by blocking type I interferon in the lupus serum and that it can be reproduced by culturing DC precursors with type I interferon. The products of plasmacytoid (lymphoid) DCs induce differentiation of myeloid DCs, thus supporting antigen presentation, and, consequently driving the pathogenic process.

In one embodiment of the invention, the therapeutic composition of the invention includes two elements (1) a Flt3L antagonist and (2) an interferon antagonist. In another embodiment of the invention, these elements can be fused together into one compound or molecule such as a fusion protein which comprises an antagonistic or competitive peptide against each Flt3L and IFN-α or another type I interferon. That is, the fusion peptide can include a portion which is a peptide that is a competitive inhibitor of the activity of Flt3L and a peptide that is a competitive inhibitor of the activity of IFN-α. In another aspect of the invention, the composition can include monoclonal antibodies against each Flt3L and IFN-α, antigen-binding fragments of each antibody (such as a CDR fragment), or a fusion protein which comprises active (antigen-binding) fragments of the antibodies. In another aspect of the invention, the composition can be comprised of a small organic molecule which is capable of interfering with the interaction between the Flt3L and its receptor and a which is capable of interfering with the activity of IFN-α. In one aspect of the invention, the composition can include the complementarity determining regions (CDRs) of monoclonal antibodies which specifically bind to Flt3L and IFN-α.

Polypeptides useful as antagonists of a type I interferon such as IFN-α or Flt3L can be polypeptides which are derived from the binding site of the respective receptor. In addition, non-functional IFN-α or Flt3L (polypeptides which compete for receptor binding, but which do not trigger a response in the receptor-bearing cell) can be synthesized. One example of such a non-functional peptide is a peptide with full capacity to bind to the receptor, but without any capacity to activate the receptor bearding cell There can be substitutions or additions or deletions to the normally occurring amino acid sequence of the polypeptides. Conservative amino acid substitutions can include: valine substituted for alanine; lysine for arginine; glutamine for asparagine; glutamate for aspartate; serine for cysteine; asparagine for glutamine, aspartate for glutamate; proline for glycine; arginine for histidine; leucine for isoleucine; arginine for lysine, leucine for methionine, leucine for phenylalanine; glycine for proline, threonine for serine; serine for threonine; tyrosine for tryptophan; phenylalanine for tyrosine and leucine for valine.

The invention provides a novel method for treating autoimmune disease, comprising blocking the ability of type I interferon to promote the generation of antigen-presenting cells. Further, the invention also provides an in vitro diagnostic assay for assessing a patient's relative risk of developing an autoimmune disease and/or monitoring a patient's disease progress. The invention provides for use of (a) an interferon antagonist that reduces activity of a type I interferon (such as reducing the binding between a type I interferon and its receptor), and (b) a Flt3 ligand (Flt3L) antagonist that reduces activity of Flt3L (such as reducing the binding between a Flt3L and its receptor) in the preparation of a composition useful for treating an autoimmune disease in a subject.

In one embodiment of the invention, the at least one interferon antagonist and the at least one Flt3L antagonist are administered at separate times to the subject. In another embodiment, they are administered simultaneously. For example, one antagonist can be administered in the morning and one in the evening. The timing or frequency of administration of the antagonists do not have to be equivalent.

As shown herein, type I interferon or type I interferon-containing serum is a necessary factor for the generation of antigen presenting cells, including but not limited to DCs. Such antigen presenting cells are shown in the present invention to drive proliferation of autologous CD4+ T cells by presenting antigens from captured apoptotic cells. In the present invention, this process of differentiation, antigen capture and antigen presentation are reduced by blocking the activity of type I interferon. This method of treatment can be used to treat autoimmune diseases by inhibiting disease progression (therapeutic application) as well as disease development in patients with an appropriate genetic background and high risk of disease development (preventive application).

Blocking of type I interferon protein and/or Flt3L includes but is not limited to using antibody (antibodies) that neutralize their ability to generate antigen-presenting cells. Blocking of type I interferon receptor or Flt3L receptor includes but is not limited to using antibodies, peptides or chemicals specifically interrupting the interaction between the ligand and its receptor(s) that leads to the generation of antigen-presenting cells. Methods for delivering the antagonists which are inhibitory (i.e., the composition of the present invention) useful in the invention include but are not limited to proteins and vectors encoding the proteins.

In one embodiment of the invention, nucleic acids encoding peptides which block function of a type I interferon and/or a Flt3L are administered to a subject. For example, virus based vectors (an example of a gene transfer vectors) can be used for delivery of these nucleic acids into the subject so that translation of the peptides occurs in vivo. The gene transfer vector may be any construct which is able to replicate within a host cell and includes, but is not limited to, plasmids, DNA viruses, retroviruses, as well as isolated nucleotide molecules. Retrovirus or adenovirus based vectors can be used, for example. Adenoviruses have attracted increasing attention as expression vectors, especially for human gene therapy (Berkner, *Curr. Top. Microbiol. Immunol.,* 158:39-66 (1992)). Such vectors contain all or a part of a viral genome, such as long term repeats ("LTRs"), promoters (e.g., CMV promoters, SV40 promoter, RSV promoter), enhancers, and so forth In any case, the vector may comprise elements of more than one virus. Examples of adenoviruses which can be employed in the present invention are well-known in the art and include more than 40 different human adenoviruses, e.g., Ad12 (subgenus A), Ad3 and Ad7 (Subgenus B), Ad2 and Ad5 (Subgenus C), Ad8 (Subgenus D), Ad4 (Subgenus E), Ad40 (Subgenus F) (Wigand et al, In: Adenovirus DNA, Doerfler, Ed., Martinus Nijhoff Publishing, Boston, pp. 408-441 (1986)). Methods for producing adenovirus vectors are well-known in the art (Berkner et al, *Nucleic Acids Res.,* 11:6003-6020 (1983); van Doren et al, *Mol. Cell. Biol.,* 4:1653-1656 (1984); Ghosh-Choudhury et al *Biochem. Biophys. Res. Commun.,* 147:964-973 (1987); McGrory et al, *Virol.,* 163:614-617 (1988); and Gluzman et al In: Eurkaryotic Viral Vectors, Ed. Gluzman, Y. pages 187-192, Cold Spring Harbor Laboratory (1982)). The resulting vectors are introduced (e.g., by transfection or by transformation, or by infection, or by injection, etc.) into a host cell which may be in vivo in the subject or in vitro. Liposome-mediated transfer of the gene transfer vector may also be carried out in the present invention.

Other examples of virus vectors that may be used for gene transfer into cells to carry out the present method of treating an autoimmune disease in a subject include, but are not limited to, retroviruses such as Moloney murine leukemia virus (MoMuLV); papoviruses such as JC, SV40, polyoma, adenoviruses; Epstein-Barr Virus (EBV); papilloma viruses, e.g. bovine papilloma virus type I (BPV); vaccinia and poliovirus; lentiviral vectors, and other human and animal virus.

Blocking of type I interferon and FLT3L signaling and/or transduction pathways useful in the invention includes, but is not limited to, using chemical agents specifically targeting relevant signaling and/or transduction pathways.

Blocking of type I interferon release and/or production useful in the present invention includes, but is not limited to, (1) blocking type I interferon synthesis by cells using specific chemical agents; (2) targeting the cells producing type I interferon so as to reduce their ability to produce type I interferon, and (3) targeting the receptors necessary to signal type I interferon production and/or release by cells so as to reduce or inhibit that production or release. In one aspect of the invention, these cells are plasmacytoid dendritic cells. In another aspect of the invention, the cells producing type I interferon which are targeted by the composition of the present invention include, but are not limited to, fibroblasts, endothelial cells and plasmacytoid dendritic cells at various stages of differentiation (e.g., bone marrow progenitors and blood precursors). Targeting a cell by a composition to reduce its function as set out above includes but is not limited to delivery of chemical agents specifically blocking differentiation of plasmacytoid dendritic cells from hematopoietic progenitors wherever such differentiation could take place.

Targeting a receptor needed to signal type I interferon production and/or release by a composition of the invention includes, but is not limited to, using a composition to block the function of mannose receptor and/or CD32 on cells.

In one aspect, the invention provides for an in vitro diagnostic assay which is useful for monitoring the status of an autoimmune disease in a subject or for identifying whether a subject is at risk for developing an autoimmune disease. The diagnostic assay includes the steps of (1) obtaining an amount of serum from the subject to be tested; (2) determining the level of Flt3L and the level of IFN-α in the subject's serum sample using any known method (e.g., using an ELISA with antibodies specific for Flt3L and for IFN-α); (3) comparing the level of Flt3L and the level of IFN-α measured in the subject's serum with the level of each factor determined to exist in a serum sample taken from an age-matched and gender-matched normal healthy subject; (4) identifying whether the levels measured from the subject to be tested are higher or lower than those of the healthy subject thereby monitoring the status of the autoimmune disease in the subject or assessing the risk of the subject for developing an autoimmune disease.

The invention is also directed to an in vitro assay for determining a subject's risk for developing an autoimmune disease which comprises (a) obtaining a serum sample from the subject; (b) quantifying IFN-α and Flt3 ligand (Flt3L) in the serum sample; and (c) comparing the quantity of IFN-α and Flt3L measured in step (b) with the quantities of IFN-α and Flt3L measured in serum taken from a healthy subject and serum taken from a subject with an autoimmune disease, thereby determining the subject's risk for developing an autoimmune disease. A high risk of developing an autoimmune disease is indicated by quantities in step (b) supra which are within a 30% range of the quantities measured for the subject with an autoimmune disease. This risk increases when quantities are 20%. In another aspect of the invention, the subjects can be age-matched.

The invention is also directed to a kit for determining a subject's risk for developing an autoimmune disease or for monitoring the status of an autoimmune disease in a subject which comprises a composition which specifically binds to Flt3L and to IFN-α in a biological sample from a subject, and wherein the composition is detectable. The detectable marker includes but is not limited to a fluorescent marker, a radioactive marker, an enzymatic marker, a calorimetric marker, a chemiluminescent marker or any combination thereof.

In one embodiment of the invention, the biological sample is a blood sample or a serum sample. In another embodiment of the invention, the composition comprises a mixture of (a) a monoclonal antibody that binds Flt3L and (b) a monoclonal antibody that binds IFN-α. In a further aspect of the invention, the kit further comprises one or more reagents for detecting and comparing amounts of the composition bound to one or more samples. In another embodiment of the invention, the kit further comprises components for correlating the quantity of composition bound to the biological sample to a relative risk of developing an autoimmune disease or a relative status of an autoimmune disease. In another embodiment of the invention, the composition is labeled with a detectable marker. The detectable marker can be, but is not limited to, a fluorescent marker, a radioactive marker, an enzymatic marker, a calorimetric marker, a chemiluminescent marker and any combination thereof. The kit can also include components for standardization or normalization among samples to insure that the diagnostic assays are comparing relatively equivalent numbers of cells or volumes of serum.

The invention provides for an in vitro assay for determining a subject's risk for developing an autoimmune disease which comprises: (a) obtaining a serum sample from the subject; (b) quantifying IFN-α and Flt3 ligand (Flt3L) in the serum sample; and (c) comparing the quantity of IFN-α and Flt3L with the quantities of IFN-α and Flt3L in serum from subjects with an autoimmune disease, thereby determining the subject's risk for developing an autoimmune disease.

In addition, the invention also provides for an in vitro assay for determining a subject's risk for developing an autoimmune disease which comprises: (a) obtaining a serum sample from the subject; (b) admixing the serum with monocytes in vitro under conditions suitable for monocyte differentiation; (c) measuring the ability of the subject's serum to induce differentiation of monocytes into dendritic cells which are capable of presenting antigen; and (d) comparing the ability measured in step (c) with (i) the ability of serum taken from a healthy subject and with (ii) the ability of serum taken from a subject suffering from an autoimmune disease, thereby determining the subject's risk for developing an autoimmune disease.

In another aspect, the present invention is an in vitro diagnostic assay by which a patient's risk of developing autoimmune disease can be determined and monitored. This diagnostic assay measures the ability of patient's serum to induce monocyte differentiation into dendritic cells in vitro in order to assess the risk that patient has for developing an autoimmune disease. In this regard, if the patient's serum induces differentiation of monocytes to dendritic cells more effectively than the known normal standard (which can be determined by using serum from several age-matched, gender-matched, healthy individuals), the assay is predictive of a disease flare in patients with autoimmune disease and/or indicative of the necessity for detailed diagnostic evaluation whether the patient is at risk of developing an autoimmune disease. In addition, the diagnostic assay is useful to monitor a patient's disease condition, if the patient has already been diagnosed with an autoimmune disease, the patient can utilize the diagnostic assay of the present invention at home, or at other convenient locations, in order to monitor the progress or improvement of the autoimmune disease and adjust his/her treatment regimen accordingly.

The effective amount of the composition will depend upon the actual composition which is used. The actual effective amount is based upon the size of the compound, the biodegradability of the compound, the bioactivity of the compound and the bioavailability of the compound. If the compound does not degrade quickly, is bioavailable and highly active, a smaller amount is required to be effective. The effective amount can be determined by one of skill in the art; it will also be dependent upon the form of the compound, the size of the compound and the bioactivity of the compound. One of skill in the art could routinely perform empirical activity tests for a compound to determine the bioactivity in bioassays and thus determine the effective amount.

This invention provides for pharmaceutical compositions including therapeutically effective amounts of polypeptide compositions and compounds, together with suitable diluents, preservatives, solubilizers, emulsifiers, adjuvants and/or carriers. Such compositions may be liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., TWEEN™ 20, TWEEN™ 80, Pluronic F68, bile acid salts), solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the compound, complexation with metal ions, or incorporation of the compound into or onto particulate preparations of polymeric compounds such as polylactic acid, polglycolic acid, hydrogels, etc, or onto liposomes, micro emulsions, micelles, unilamellar or multi lamellar vesicles, erythrocyte ghosts, or spheroplasts. Such compositions will influence the physical state, solubility, stability, rate of in vivo release, and rate of in vivo clearance of the compound or composition. The choice of compositions will depend on the physical and chemical properties of the composition.

Controlled or sustained release compositions include formulation in lipophilic depots (e.g., fatty acids, waxes, oils).

Also comprehended by the invention are particulate compositions coated with polymers (e.g., poloxamers or poloxamines) and the therapeutic composition coupled to antibodies directed against tissue-specific receptors, ligands or antigens or coupled to ligands of tissue-specific receptors or any other tissue-or cell-targeting peptide. Other embodiments of the therapeutic compositions of the invention incorporate particulate forms protective coatings, protease inhibitors or permeation enhancers for various routes of administration, including parenteral, pulmonary, nasal and oral.

When administered, compounds are often cleared rapidly from the circulation and may therefore elicit relatively short-lived pharmacological activity. Consequently, frequent injections of relatively large doses of bioactive compounds may by required to sustain therapeutic efficacy. Compounds modified by the covalent attachment of water-soluble polymers such as polyethylene glycol (PEG), copolymers of polyethylene glycol and polypropylene glycol, carboxymethyl cellulose, dextran, polyvinyl alcohol, polyvinylpyrrolidone or polyproline are known to exhibit substantially longer half-lives in blood following intravenous injection than do the corresponding unmodified compounds. Such modifications may also increase the compound's solubility in aqueous solution, eliminate aggregation, enhance the physical and chemical stability of the compound, and greatly reduce the immunogenicity and reactivity of the compound. As a result, the desired in vivo biological activity may be achieved by the administration of such polymer-compound adducts less frequently or in lower doses than with the unmodified compound.

Attachment of polyethylene glycol (PEG) to compounds is particularly useful because PEG has very low toxicity in mammals (Carpenter et al., 1971). For example, a PEG adduct of adenosine deaminase was approved in the United States for use in humans for the treatment of severe combined immunodeficiency syndrome. A second advantage afforded by the conjugation of PEG is that of effectively reducing the immunogenicity and antigenicity of heterologous compounds. For example, a PEG adduct of a human peptide might be useful for the treatment of disease in other mammalian species without the risk of triggering a severe immune response. The polypeptide or composition of the present invention may be delivered in a microencapsulation device so as to reduce or prevent an host immune response against the polypeptide or against cells which may produce the polypeptide. The polypeptide or composition of the present invention may also be delivered microencapsulated in a membrane, such as a liposome.

As an example, polymers such as PEG may be conveniently attached to one or more reactive amino acid residues in a peptide of the therapeutic composition such as the alpha-amino group of the amino terminal amino acid, the epsilon amino groups of lysine side chains, the sulfhydryl groups of cysteine side chains, the carboxyl groups of aspartyl and glutamyl side chains, the alpha-carboxyl group of the carboxy-terminal amino acid, tyrosine side chains, or to activated derivatives of glycosyl chains attached to certain asparagine, serine or threonine residues.

Numerous activated forms of PEG suitable for direct reaction with proteins have been described. Useful PEG reagents for reaction with protein amino groups include active esters of carboxylic acid or carbonate derivatives, particularly those in which the leaving groups are N-hydroxysuccinimide, p-nitrophenol imidazole or 1-hydroxy-2-nitrobenzene-4-sulfonate. PEG derivatives containing maleimido or haloacetyl groups are useful reagents for the modification of protein free sulfhydryl groups. Likewise, PEG reagents containing amino hydrazine or hydrazide groups are useful for reaction with aldehydes generated by periodate oxidation of carbohydrate groups in proteins.

In one preferred embodiment the pharmaceutical carrier may be a liquid and the pharmaceutical composition would be in the form of a solution. In another equally preferred embodiment, the pharmaceutically acceptable carrier is a solid and the composition is in the form of a powder or tablet. In a further embodiment, the pharmaceutical carrier is a gel and the composition is in the form of a suppository or cream. In a further embodiment the active ingredient may be formulated as a part of a pharmaceutically acceptable transdermal patch.

A solid carrier can include one or more substances which may also act as flavoring agents, lubricants, solubilizers, suspending agents, fillers, glidants, compression aids, binders or tablet-disintegrating agents; it can also be an encapsulating material. In powders, the carrier is a finely divided solid which is in admixture with the finely divided active ingredient. In tablets, the active ingredient is mixed with a carrier having the necessary compression properties in suitable proportions and compacted in the shape and size desired. The powders and tablets preferably contain up to 99% of the active ingredient. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Liquid carriers are used in preparing solutions, suspensions, emulsions, syrups, elixirs and pressurized compositions. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators. Suitable examples of liquid carriers for oral and parenteral administration include water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the carrier can also be an oily ester such as ethyl oleate and isopropyl myristate. Sterile liquid carriers are useful in sterile liquid form compositions for parenteral administration. The liquid carrier for pressurized compositions can be halogenated hydrocarbon or other pharmaceutically acceptable propellent.

Liquid pharmaceutical compositions which are sterile solutions or suspensions can be utilized by for example, intramuscular, intrathecal, epidural, intraperitoneal or subcutaneous injection. Sterile solutions can also be administered intravenously. The active ingredient may be prepared as a sterile solid composition which may be dissolved or suspended at the time of administration using sterile water, saline, or other appropriate sterile injectable medium Carriers are intended to include necessary and inert binders, suspending agents, lubricants, flavorants, sweeteners, preservatives, dyes, and coatings.

The active ingredient of the therapeutic composition of the present invention (i.e., the Flt3L antagonist and the interferon antagonist) can be administered orally in the form of a sterile solution or suspension containing other solutes or suspending agents, for example, enough saline or glucose to make the solution isotonic, bile salts, acacia, gelatin, sorbitan monoleate, polysorbate 80 (oleate esters of sorbitol and its anhydrides copolymerized with ethylene oxide) and the like.

The active ingredient can also be administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

The practice of the present invention will employ, unless otherwise indicated, conventional techniques of molecular biology, microbiology, recombinant DNA technology, and immunology, which are within the skill of the art. Such techniques are explained in the literature: See, e.g., Sambrook, Fritsch & Maniatis, Molecular Cloning: A Laboratory Manual, Second Edition (1989); DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); and Handbook of Experimental Immunology, Vols. I-IV (D. M. Weir and C. C. Blackwell eds., 1986, Blackwell Scientific Publications).

As used herein, the word "or" means any one member of a particular list and also includes any combination of members of that list.

As used herein, the singular forms "a," "an" and "the" include plural references unless the content clearly dictates otherwise.

The invention will be further described with reference to the following examples; however, it is to be understood that the invention is not limited to such examples. Rather, in view of the present disclosure which describes the current best mode for practicing the invention, many modifications and variations would present themselves to those of skill in the art without departing from the scope and spirit of this invention. All changes, modifications, and variations coming within the meaning and range of equivalency of the claims are to be considered within their scope.

EXAMPLE 1

Figure 2E:
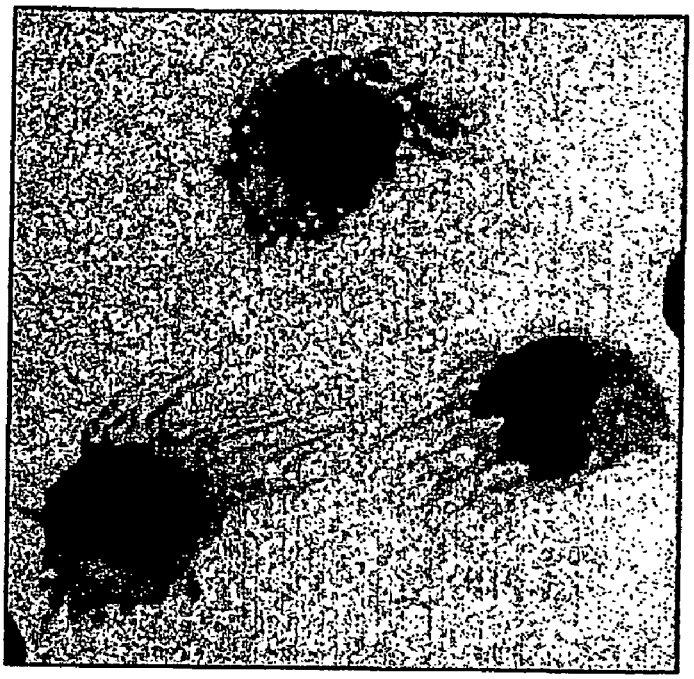
Figure 2D:
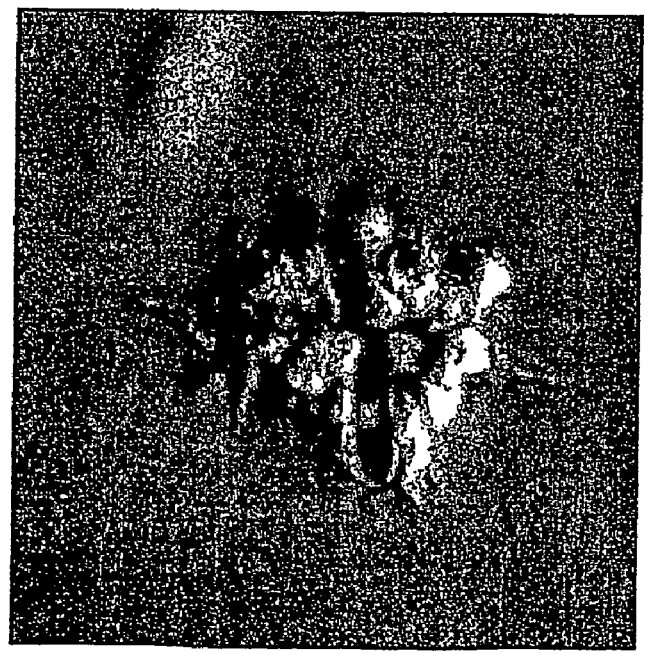

SLE Sera Induces Monocytes to Differentiate into Cells with Properties Like Dendritic Cells Normal monocytes were exposed to SLE sera in vitro: within 12-24 hours, clustering of monocytes was noted; and within 24-48 hours, clustered cells displayed fine cytoplasmic projections reminiscent of DC cultures (FIGS. 2A and 2B). Only SLE serum induced monocytes to cluster with 12-24 hours and acquire veiled cell morphology (FIGS. 2A-2B compared to AS in FIG. 2C).

SLE serum: After informed consent, blood was obtained from the patient who satisfied diagnostic criteria of American College of Rheumatology (ACR) for SLE. Whole blood was collected into tubes containing EDTA or heparin, and was separated immediately by centrifugation at 100×g at 4° C. The plasma was harvested, treated with thrombin (Jones Pharma Incorporated, MO) and stored at −80° C. until used. Disease activity was assessed by using the SLE Disease Activity Index (SLEDAI) score (Lahita, R. G. 1999. Systemic Lupus Erythematosus. *Academic Press* 3rd edition) determined on the same day that the blood specimen was obtained.

Cell culture and phenotypic analysis: Monocytes were isolated from blood mononuclear cells, after Ficoll-Paque™ gradient, by depletion of T-cells, B-cells and NK cells using purified anti-CD3, anti-CD19, anti-CD56 and anti-glycophorin A antibodies followed by immunomagnetic depletion (Dynabeads). Enriched CD14+monocytes were cultured in 6 well plates ($1\times10^6$/well) for 3 days in the presence of GM-CSF at 100 ng/mL and IFN-α at 1000 UI/mL; or GM-CSF at 100 ng/mL and IL-4 at 20 ng/mL; or lupus serum; or autologous serum On Day 3, cells were harvested and stained with anti-CD14-PE antibody, anti-CD83-PE antibody, anti-HLA-DR-PrCP (peridnine chlorophyll protein) antibody, anti-mannose-receptor-PE antibody, anti-CD80 PE (phycoerythrin) antibody, anti-CD86-PE antibody, anti-CD40 PE antibody, anti-CD16-PE antibody, anti-CD32 PE antibody, anti-CD64-PE antibody and anti-CD1a-FITC antibody.

Figure 3:
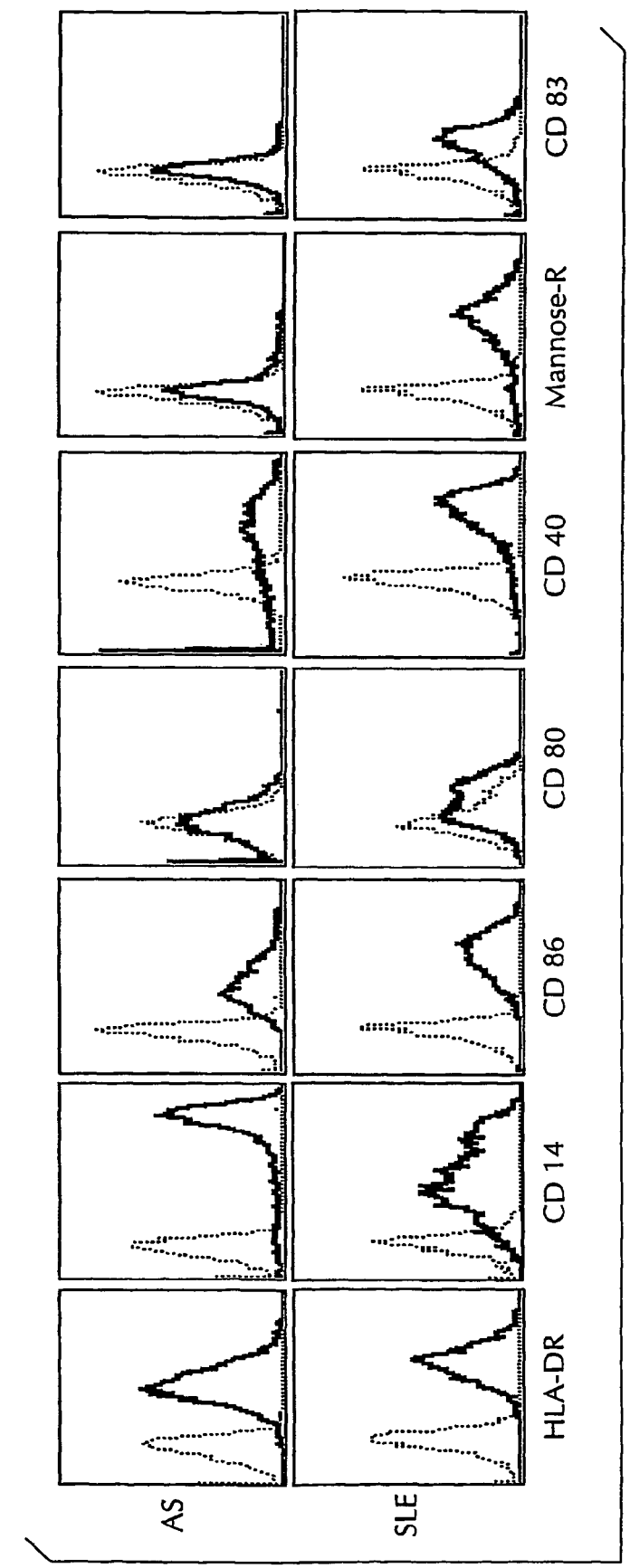
FIG. 3 is a graphic illustration showing results from a flow cytometry analysis of monocytes cultured with SLE serum which acquire the phenotype of mature DCs. Each graph shows an increase in detection of a labeled antibody which is specific for the cell surface markers listed below each graph. Monocytes cultured with SLE serum (lower panel) but not those cultured with autologous serum (upper panel) down-regulate CD14 expression, up-regulate the expression of HLA-DR and co-stimulatory molecules such as CD86, CD80 and CD40 and acquire expression of CD83, a marker of mature DCs. Horizontal axis represents fluorescence intensity in a log scale for an isotype control (dotted lines) and a specific antibody (solid lines). Vertical axis represents relative cell frequency.
Figure 4:
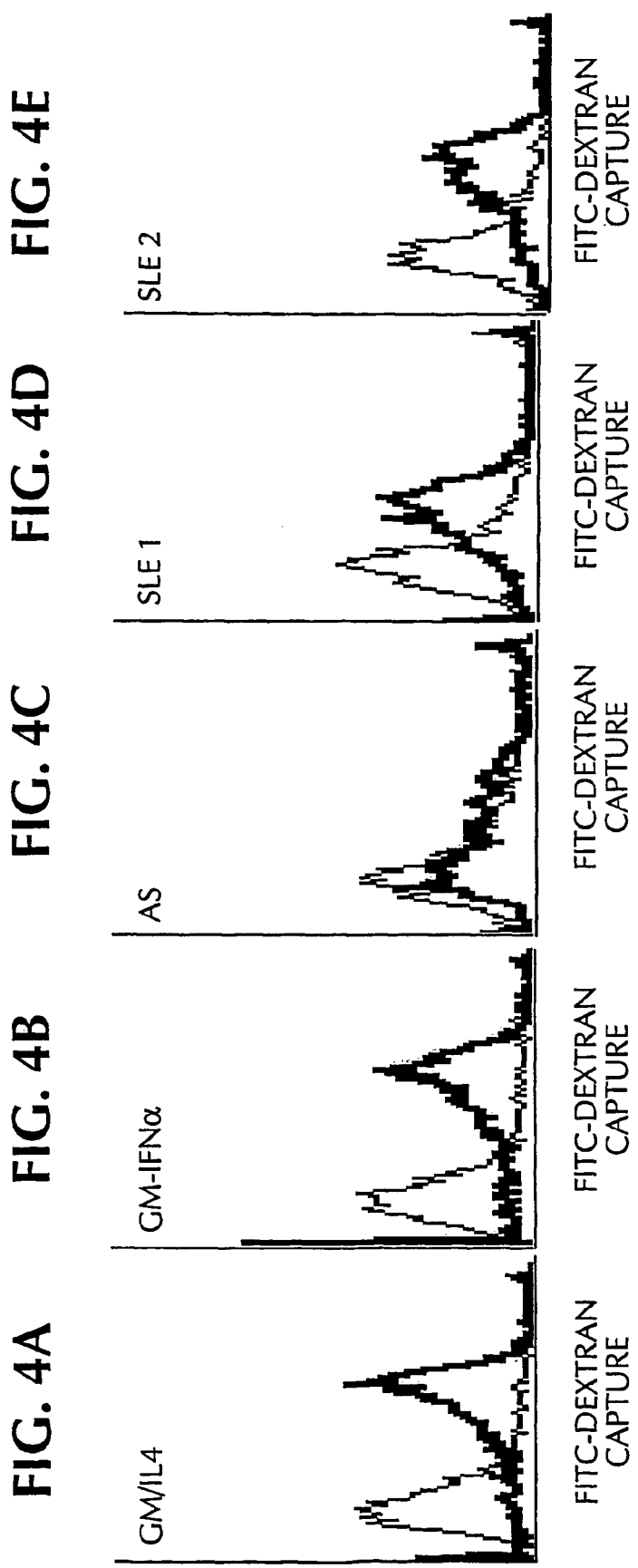
FIGS. 4A-4E are graphic illustrations of flow cytometry results showing that monocytes cultured with SLE serum capture soluble antigens. Enriched monocytes were cultured with SLE serum (FIGS. 4D and 4E) (SLE 1 and SLE2 denote serum from two different patients with SLE) or with AS serum (FIG. 4C) and their endocytic activity was determined using FITC-dextran (FITC-DX) uptake at 4° C. (thin-line) and 37° C. (thick-line). Monocytes cultured with GM-CSF and IFN-α ("GM-IFNα") (FIG. 4B) as well as those cultured with GM-CSF and IL-4 ("GM/IL-4") (FIG. 4A) (which is a standard for in vitro DC cultures) exhibit comparable levels of FITC-DX uptake. Monocytes cultured with AS serum do not take up FITC-DX.

Enriched CD14+ monocytes from normal donor were cultured ($1\times10^6$/well) with 20% lupus serum or autologous serum. Monocytes were cultured with SLE-DCs and on Day 3, cells were harvested and evaluated by flow cytometry for expression of certain cell surface molecules. Flow cytometry analysis demonstrated down-regulation of CD14, increased expression of MHC class II, costimulatory molecules: CD40, CD86 and CD80, CD83 as well as mannose-receptor, CD32 and CD36 (FIG. 3). Induction of monocyte differentiation to cells with the morphology and phenotype of DCs, rather than macrophages (MΦ), was restricted to those DCs grown in SLE serum Indeed, neither autologous nor allogeneic serum induce such phenotype (FIG. 2C).

Monoclonal antibodies (mAbs) to the following antigens were utilized: CD14, HLA-DR (Becton Dickinson); CD86, CD40, HLA-ABC, CD1a (Dako, Carpinteria, Calif.); CD80, CD83 (Beckman Coulter/Immunotech, New York).

Since SLE serum-induced cells displayed antigen capture receptors and since the ability to capture antigens is an important property of DCs, it was determined whether the cells differentiated in culture could capture soluble antigens. To this end, SLE serum cultured monocytes were incubated with FITC-Dextran. As shown in FIGS. 4A-4E, SLE serum-induced cells were as efficient as GM-CSF/IL-4 induced DCs in the uptake of FITC-Dextran.

The endocytic activity of the cells differentiated in culture was determined by incubating the cells with 100 μg/mL FITC-Dextran for 1 hour at 37° C. As a control, some cells were incubated with FITC-Dextran on ice. The cells were washed with cold PBS/FCS and analyzed by flow cytometry.

Thus, morphology, phenotype and antigen capture indicated that SLE serum directs monocytes to differentiate into cells capable of capturing antigens, i.e., expressing antigen capture molecules such as CD14, mannose receptor and CD36 (characteristic of immature DCs and MΦ), and expressing molecules important for antigen presentation including HLA-DR, co-stimulatory molecules and CD83, a marker of mature DCs.

Figure 5:
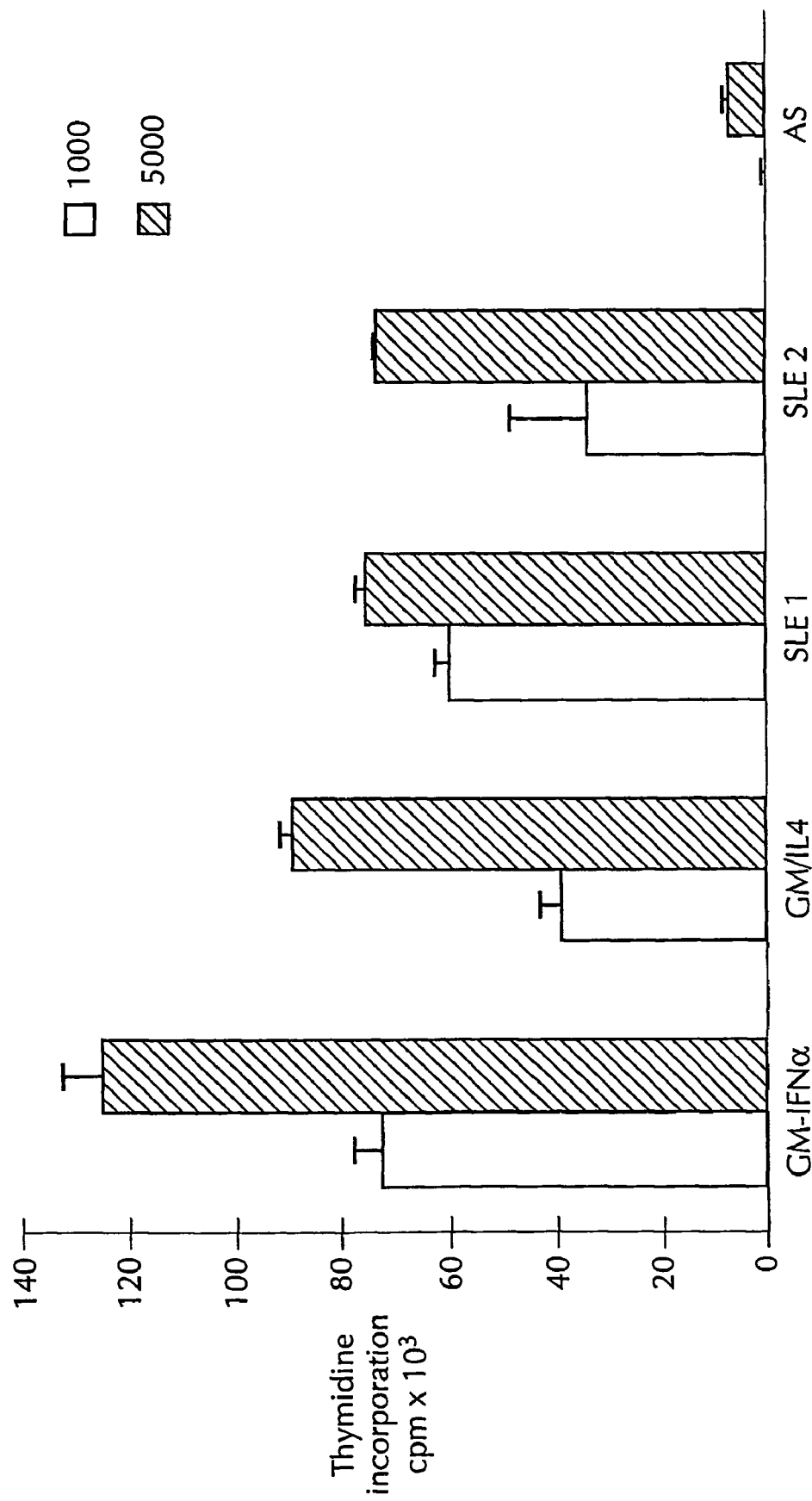
FIG. 5 is a histogram showing that monocytes cultured with SLE serum, but not those cultured with AS serum induce proliferation of allogeneic naive CD4+ T cells. Monocytes cultured with GM/IFNα, GM/IL-4, SLE 1, SLE 2, and AS serum were washed and cultured at graded doses (1000 cells and 5000 cells) with $1\times10^5$ näive CD4+CD45RA+ allogeneic T lymphocytes for 5 days. T cell proliferation was determined by thymidine incorporation (cpm×$10^3$, vertical axis).
Figure 6:
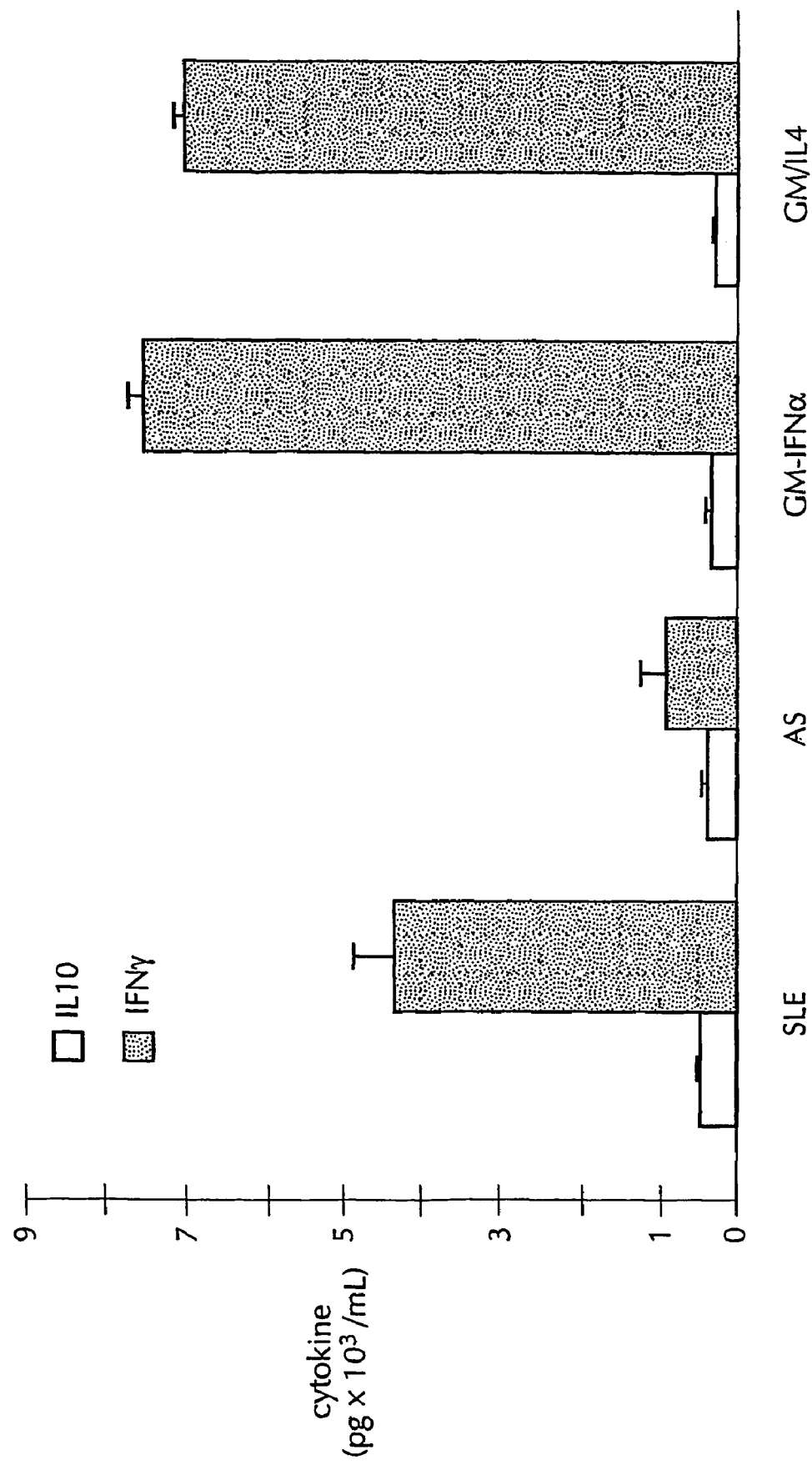
FIG. 6 is a graphic illustration of the level of T cell cytokines produced by T cells induced by either SLE-DCs or DCs cultured in AS serum. Cytokine release was assayed by an ELISA assay and IL-10 and IFN-γ are shown in pg×10³/mL on the vertical axis.

It was next determined whether monocytes cultured with SLE serum were able to induce proliferation of naïve CD4+ T cells, a property unique to DCs among all antigen presenting cells. As shown in FIG. 5, monocytes cultured with autologous serum induced a limited proliferation of allogeneic CD4+ T lymphocytes whereas monocytes cultured with SLE serum induced a strong T cell proliferation similar to that of GM-CSF/IL-4 DCs, which is a standard characteristic of DCs in vitro. FIG. 6 illustrates the level of T cell cytokines produced by T cells induced by either SLE-DCs or DCs cultured in AS serum SLE-DCs induced T cells to produce IFN-γ and not IL-10 (except at negligible levels), thus demonstrating a type I polarization (Th1). Monocytes cultured with either SLE serum, AS serum, GM-CSF/IFN-α or GM-CSF/IFN-α were washed and plated with allogeneic CD4+ T cells. Supernatants were harvested 5 days after culture, and overnight restimulation with PHA. Cytokine release was assayed by an ELISA assay and IL-10 and IFN-γ are shown in $pg\times10^3$/mL on the vertical axis. Thus, the activated CD4+ T lymphocytes secreted high levels of interferon-γ, low levels of IL-10 and no IL-4 consistent with type I polarization.

T-cell proliferation and cytokine assay: DCs were cultured with $1\times10^5$ freshly isolated CD4+ allogeneic T cells at graded doses for 5 days in cRPMI plus 10% human AB serum or with naïve CD4+CD45RA+ allogeneic T lymphocytes. To assay autologous T cell proliferation, GM-CSF/IFN-α or GM-CSF/IL-4 or lupus-cells were pulsed with DNA-bodies for 4 hours and cultured with $1'10^5$ autologous T cells at graded doses. Cells were pulsed for the last 16 hours with 0.5 μCi [$^3$H] thymidine per well (New England Nuclear, Boston, Mass.). For cytokine analysis, supernatants were harvested 5 days after culture, and the cells were restimulated with PHA in fresh medium for 24 hours. Release of cytokines was assayed by ELISA kits (R&D Systems, Minneapolis, Minn.).

EXAMPLE 2

SLE-DCs Present Antigens from Captured Apoptotic Cells

The non-normal and inappropriate processing of apoptotic cells by the immune system is considered as one of the pathogenic events in SLE. Thus, it was next determined whether SLE-DCs can present antigens from captured apoptotic cells. To this end, SLE-DCs were shown to be able to capture apoptotic cell fragments in culture (FIGS. 7A-7B).

Figure 8B:
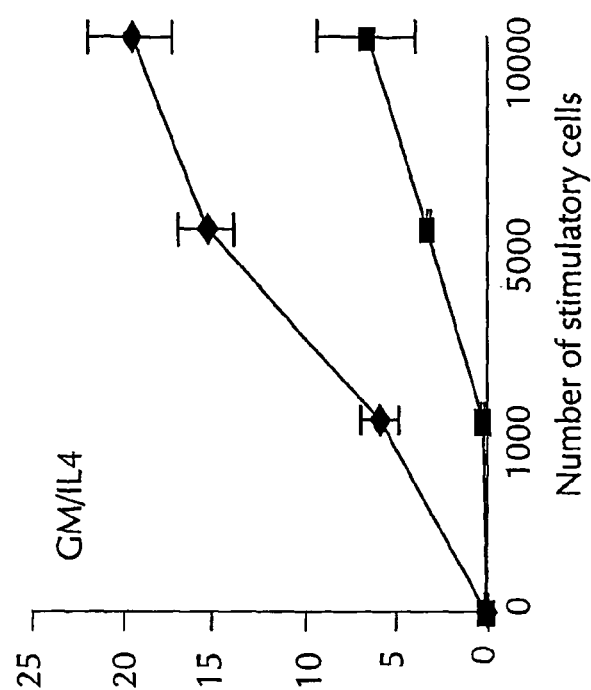
FIGS. 8A and 8B are graphic illustrations showing the capture of allogeneic apoptotic cells and presentation of their antigens to autologous CD4+ T cells.
Figure 8A:
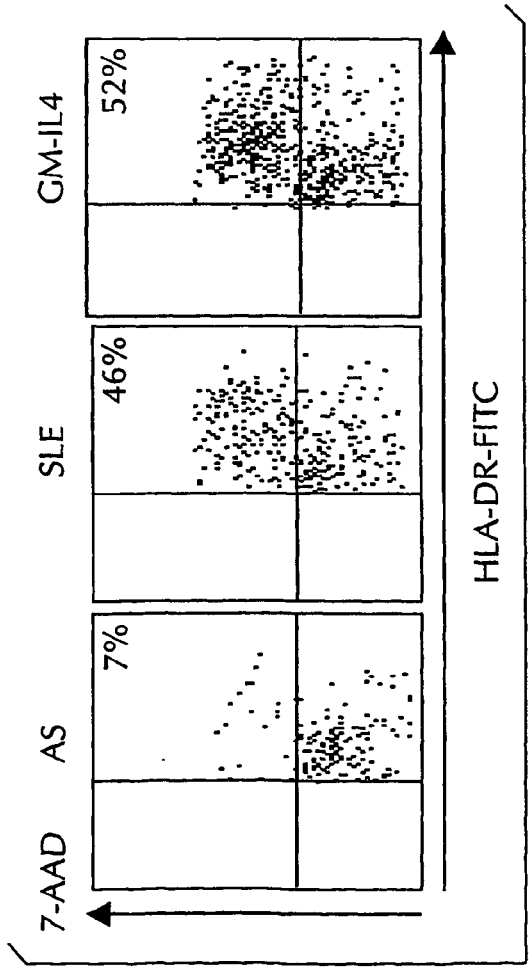

SLE-DCs could also capture DNA containing apoptotic bodies derived from melanoma cells. FIGS. 8A and 8B show the capture of allogeneic apoptotic cells and presentation of their antigens to autologous CD4+ T cells. SLE-DCs captured DNA containing apoptotic bodies (FIG. 8A) and presented their antigens to autologous CD4+ T cells as indicated by the induction of CD4+ T cell proliferation (FIG. 8B). HLA-DR+ monocytes induced by AS serum, SLE serum and GM-CSF/IL-4 captured 7AAD labeled DNA-bodies (melanoma cell line killed by gamma-irradiation (150 Gy)). To allow capture of apoptotic bodies, antigen presenting cells are admixed with killed cells and incubated for 1 hour at 37° C. Thereafter, these loaded SLE-DCs were sorted by flow cytometry and cultured with autologous CD4+ T cells. T cell proliferation is determined after 5 days.

These loaded SLE-DCs were then cultured with autologous CD4+ T cells. As shown in FIG. 8B, loaded SLE-DCs were able to induce proliferation of autologous CD4+ T cells. Thus, SLE sera induced monocytes to differentiate into functional DCs which are able to capture and present antigens processed from apoptotic cells.

EXAMPLE 3

Only IFN-α Containing Active SLE Sera Induce Monocytes to Become SLE-DCs

Figure 9B:
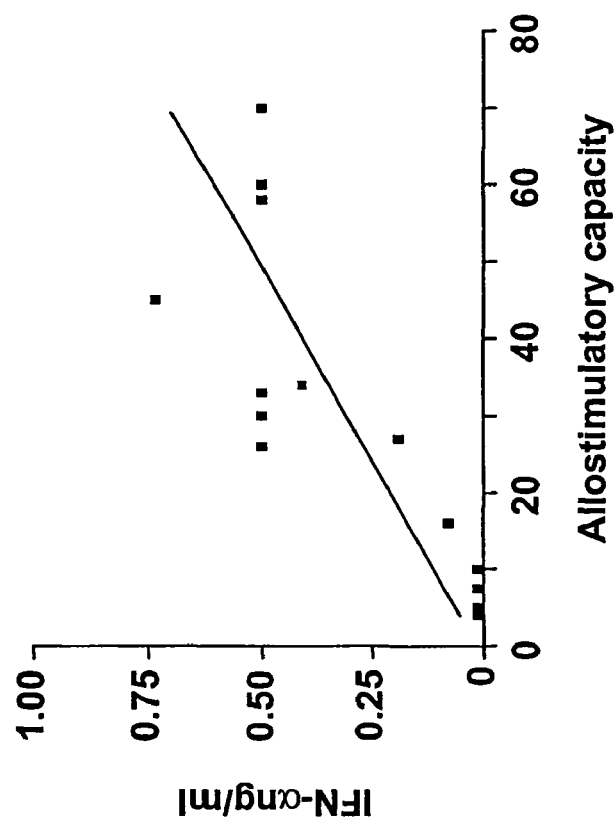
FIGS. 9A-9B are graphic illustrations showing the relation of SLE disease activity to the IFN-α inducing activity of SLE-DCs.
Figure 9A:
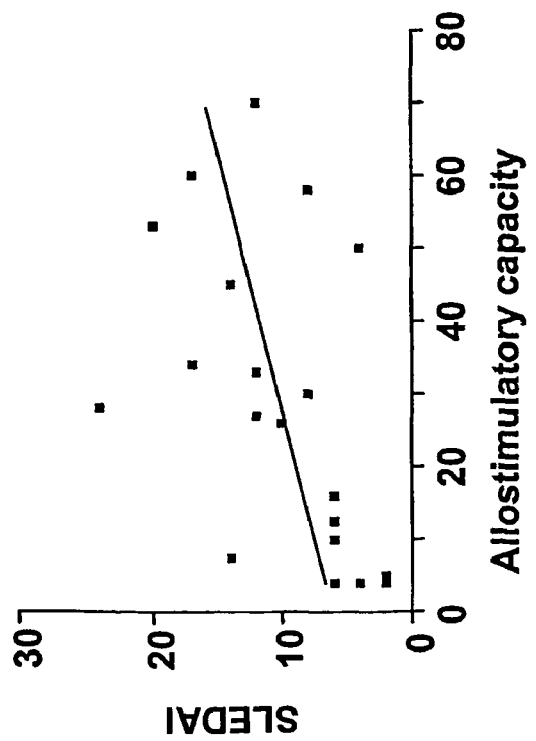

Experiments were performed to determine whether all SLE sera were able to direct monocyte differentiation into DCs. Monocytes were cultured with 19 different SLE sera to be tested for their ability to stimulate a mixed leukocyte response or mixed lymphocyte reaction (MLR). As shown in Table 1, monocytes cultured with autologous serum were only able to induce very low T cell proliferation (negative control), and monocytes cultured with GM-CSF/IL-4 to produce DCs elicited a 100% MLR (positive control), the mean proliferation was 7.5% (±6.4%, n=5). When monocytes cultured with SLE sera were evaluated in the same way, considering 20% proliferation as a cut-off point (mean+2SD of autologous serum cultured monocytes) 11 of the 19 sera induced monocytes to become allostimulatory DCs with mean proliferation of 41%±15%. As sera from patients with dermatomyositis were unable to reproduce this skewing and since the patients with dermatomyositis were treated with the same steroid regimen as SLE patients, it was concluded that the effects of SLE sera were independent of the steroids. Furthermore, sera from two newly diagnosed untreated patients efficiently differentiated monocytes into SLE-DCs. Importantly, of those 11 sera that induced SLE-DCs, 7 sera that were tested for the IFN-α levels contained more than 190 pg/mL IFN-α, while most of other sera unable to induce SLE-DCs contained less IFN-α than could be detected in the assay (12 pg/mL) (Table 1). Furthermore, the DCs inducing capacity of SLE sera was related to the disease activity. In FIGS. 9A-9B, a graph shows the relation of SLE disease activity to the inducing activity of SLE-DCs. Monocytes were cultured with 11 different SLE sera taken from either patients with active lupus (SLE Disease Activity Index (SLEDAI)>6) or inactive lupus (SLEDAI<6), and the generated cells were tested for their ability to induce T cell proliferation. As controls, monocytes were cultured with GM-CSF and IL-4. The vertical axis shows the percent of induced allostimulatory capacity. Therefore, the ability of SLE sera to skew monocyte differentiation toward DCs was disease-specific and correlated with the levels of IFN-α.

TABLE 1

IFN-α containing SLE sera induce monocytes to acquire the capacity to stimulate mixed lymphocyte reaction.

| SERUM | MLR | IFN-α level pg/ml | SLEDAI |
|---|---|---|---|
| SLE 1 | 53% | ND | 20 |
| SLE 2 | 58% | >500 | 8 |
| SLE 3 | 27% | 192 | 12 |
| SLE 4 | 28% | ND | 24 |
| SLE 5 | 33% | >500 | 12 |
| SLE 6 | 5% | <12.5 | 2 |
| SLE 7 | 45% | 733 | 14 |
| SLE 8 | 34% | 410 | 17 |
| SLE 9 | 26% | >500 | 10 |
| SLE 10 | 4% | <12.5 | 6 |
| SLE 11 | 12.5% | 25 | 6 |
| SLE 12 | 70% | >500 | 12 |
| SLE 13 | 4% | <12.5 | 4 |
| SLE 14 | 50% | ND | 4 |
| SLE 15 | 10% | <12.5 | 6 |
| SLE 16 | 16% | 78 | 6 |
| SLE 17 | 30% | >500 | 8 |
| SLE 18 | 60% | >500 | 17 |
| SLE 19 | 7.5% | <12.5 | 14 |
| SLE 20 | 4% | <12.5 | 2 |
| AS (n = 8) | 7% | <12.5 | |
| Juvenile arthritis (n = 2) | 3% | <12.5 | |
| Dermatomyositis (n = 3)* | 4% | <12.5 | |
| GM/IL4 | 100% | | |

Monocytes were cultured with different SLE sera (Table 1, column 1) and the generated cells were tested for their ability to induce allogeneic T cell proliferation (Mixed lymphocyte reaction {column 2, Table 1, MLR}). As controls, monocytes were cultured with GM-CSF and IL-4 and used as a 100% standard. The allostimulatory activity of monocytes cultured with SLE serum is expressed as a percentage of T cell proliferation as compared to GM-CSF and IL-4 and related to levels of IFN-α in the serum (column 3, Table 1) and to disease activity (SLEDAI, column 4, Table 1). SLEDAI consists of 9 groups of clinical and laboratory criteria which include assessment of organ systems: CNS, vascular, renal, musculoskeletal, serosal, dermal, immunologic and hematologic. ND denotes not done, AS denotes autologous serum from healthy donors, SLE denotes serum from patients with SLE.

EXAMPLE 4

The Ability of SLE Sera to Induce SLE-DCs is Abolished by Blocking IFN-α

Figure 10:
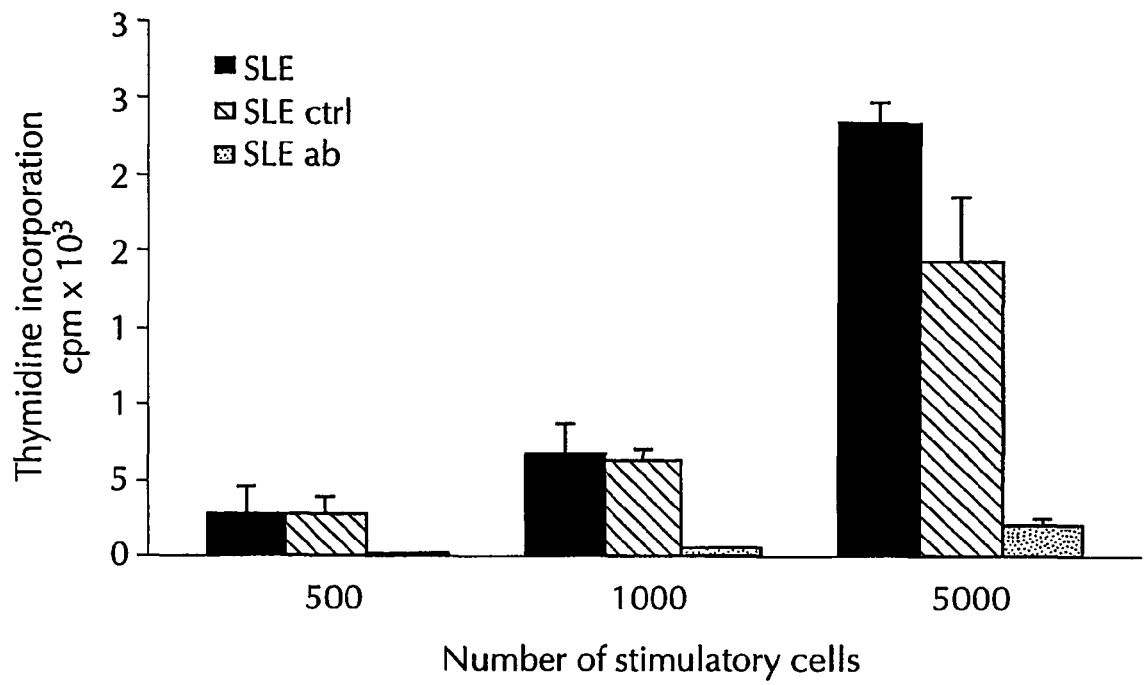
FIG. 10 is a graphic illustration showing the blocking of IFN-α in serum obtained from SLE patients. Antigen presenting cells are generated with SLE serum without or with adding an isotype control or antibody neutralizing IFN-α as indicated on the graph. The cells are washed and cultured as stimulatory cells, at indicated doses, with purified allogeneic CD4+ T cells (1×10⁵) for 5 days. T cell proliferation was determined by thymidine incorporation (cpm×10³, vertical axis).

The ability of the DCs to skew the differentiation of monocytes toward the generation of antigen-presenting cells was related to the level of IFN-α in SLE serum The phenotype of SLE-DCs was reminiscent of that induced by GM-CSF and IFN-α and therefore, SLE sera were pre-incubated with an anti-IFN-α neutralizing antibody. The cells cultured with such sera were tested for their ability to induce the differentiation of monocytes into DCs as measured by their ability to induce MLR. The ability of SLE sera to induce functional DCs was inhibited by neutralization of IFN-α, but not by the isotype control (as shown in FIG. 10) nor other blocking antibodies to IL-4, CD40-L and IL-10, which indicates that IFN-α is necessary for the induction of SLE-DCs. FIG. 10 illustrates the blocking of IFN-α in monocyte cell cultures serum obtained from SLE patients. The addition of an interferon blocking antibody resulted in a much decreased ability to induce the proliferation of allogeneic CD4+ T cells. The results show that DCs inducing activity of SLE serum is dependent on IFN-α and is abolished by blocking IFN-α in SLE serum used to culture monocytes. Purified monocytes were cultured with SLE serum, or serum pre-incubated for 30 min at saturating concentration of IFN-α blocking Ab (SLE ab) (Biosource) or with the corresponding concentration of isotype control (SLE ctrl). After three days, the cells were assessed for their ability to induce the proliferation of allogeneic CD4+ T-cells.

EXAMPLE 5

Patients with SLE Have High Serum Levels of IFN-α

Figure 11:
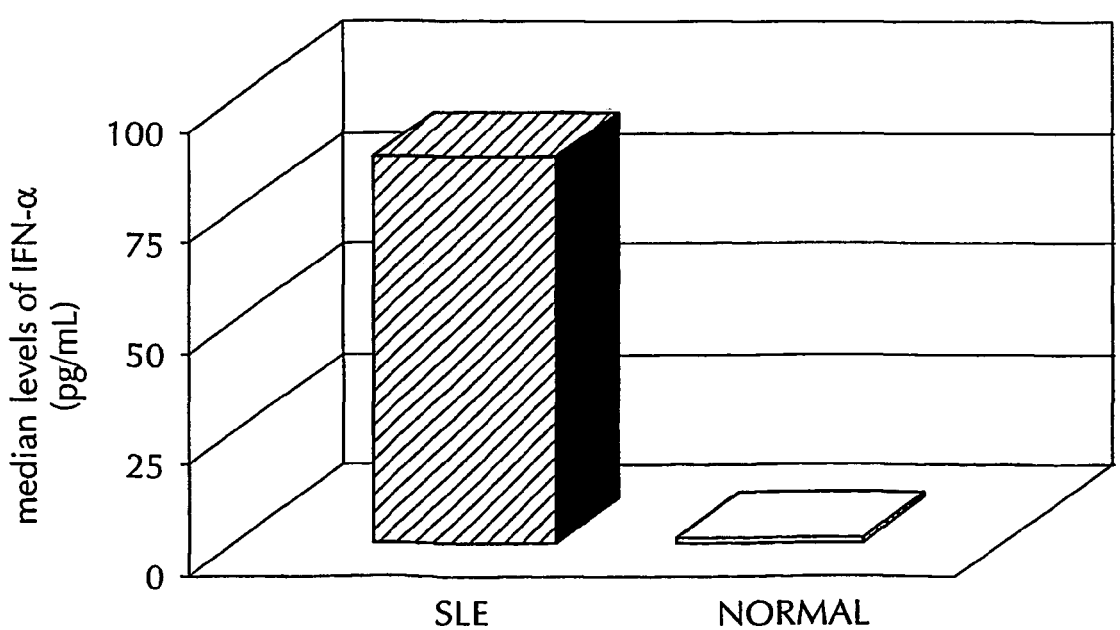
FIG. 11 shows that patients with SLE have high serum levels of IFN-α. Serum samples were taken from 45 patients with SLE and 28 normal patients.

Serum levels of IFN-α in pediatric SLE patients was determined. As shown in FIG. 11, serum taken from SLE patients had much higher levels of IFN-α than serum obtained from healthy subjects (controls). Serum was obtained from patients with SLE. The serum was assayed for IFN-α using an ELISA kit (BioSource, according to manufacturer's recommendations) which is based on the international reference standard for human interferon (approved by National Institutes of Health). The calorimetric reaction was developed using HRP and TNB. Absorbances at 450 nm were determined with a microplate reader. The assay's extended range protocol was used which allowed determination of serum levels in the range from 10 to 5000 pg/mL.

EXAMPLE 6

PBMC SLE Patients Can Secrete IFN-α in Response to Viral Triggering

Figure 12:
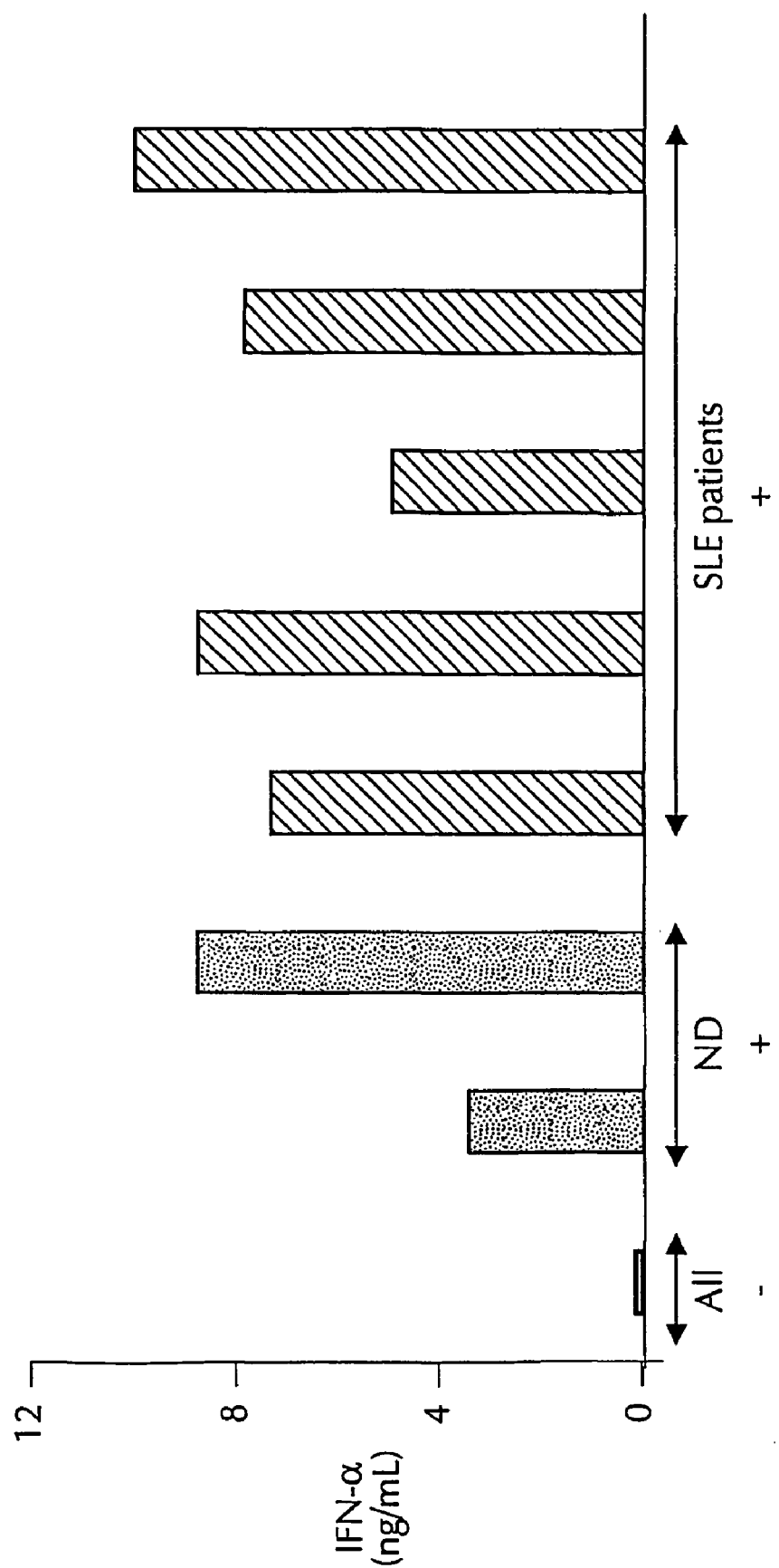
FIG. 12 is a graphic illustration showing that peripheral blood mononuclear cells (PBMCs) from patients with SLE secrete IFN-α in vitro in response to viral triggering. Total PBMCs were cultured in 96-well plates with or without influenza virus (10 µg/mL). Supernatants were harvested after culturing for 24 hours and assayed for IFN-α release by ELISA. "All –" represents levels in control cultures without virus. "+" denotes cultures with virus. "ND" denotes normal donor.

When exposed to influenza virus, PBMCs from SLE patients released high levels of IFN-α when compared to the level of IFN-α released from PBMCs from healthy adults which were exposed to influenza virus (see FIG. 12).

EXAMPLE 7

IFN-α Induces BAFF/Blys Expression on Monocytes and BCMA Expression on PBMC

Figure 13B:
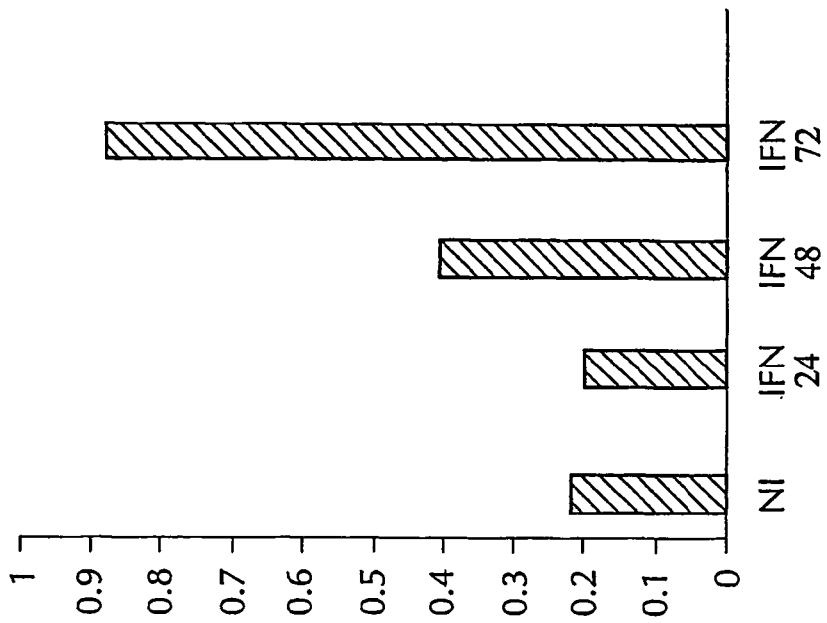
FIGS. 13A and 13B is a graphic illustration showing that IFN-α induces in vitro BAFF/Blys (B cell activating factor of the TNF family)/Blys (B lymphocyte stimulator) expression on monocytes and BCMA (B cell maturation antigen) expression on PBMCs.
Figure 13A:
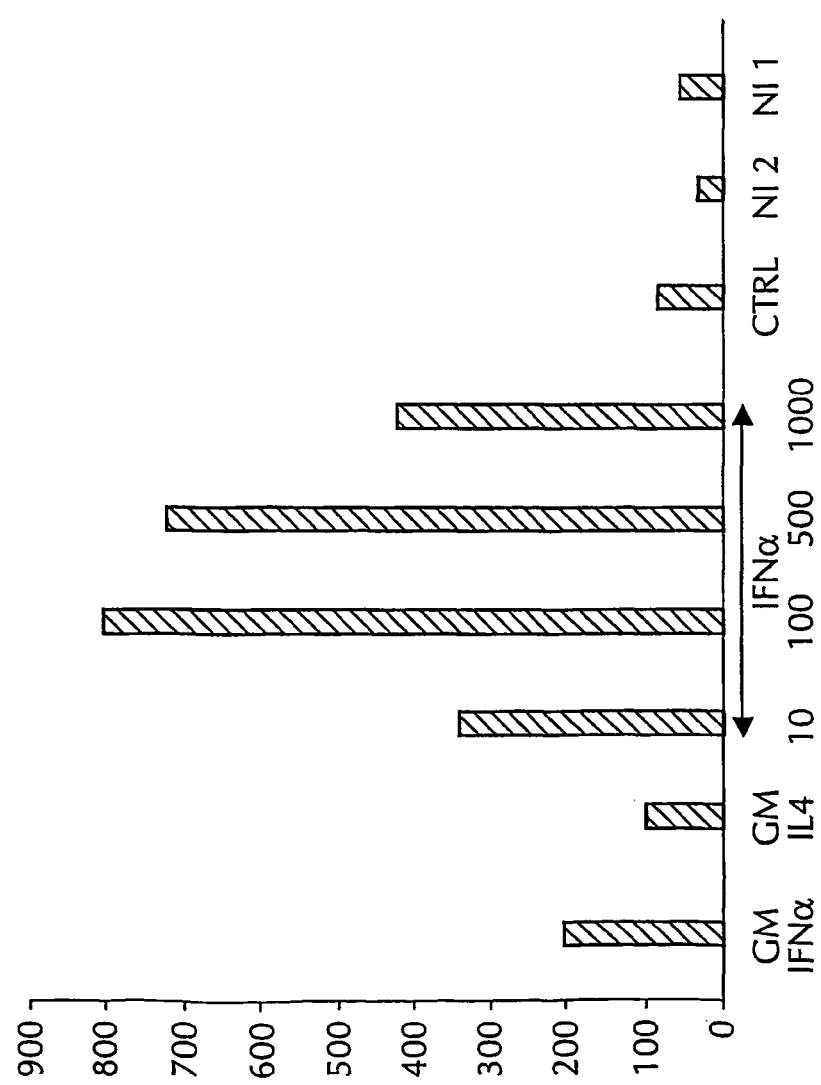

A novel member of the TNF family, designated BAFF/Blys-L (for B-cell activating factor belonging to the TNF family), is found on DCs and T-cells and binds to two receptors on B-cells, namely, BCMA and TACI, and induces their proliferation and immunoglobulin secretion. Therefore, it was determined whether IFN-α would regulate the expression of both molecules (i.e., BCMA and TACI) on the respective cell types. As shown in FIGS. 13A-13B, IFN-α, but not other factors, induces high levels of BAFF/Blys in monocytes as determined by real-time PCR. Furthermore, IFN-α induces BCMA expression on normal PBMCs.

EXAMPLE 8

Screening Patient Serum for Induction of Monocyte Differentiation in Vitro Diagnostic Assay Serum from a patient is screened for its ability to induce monocyte differentiation to dendritic cells which differentiation can then be blocked by neutralizing type I interferon.

Following the procedures outlined in detail in Example 1, patient serum was obtained. Following the procedures outlined in Example 1, an aliquot of patient serum is added to an aliquot of purified monocytes from normal patients. After about three days, the degree of differentiation of the monocytes to dendritic cells is assessed by any means known in the art. Exemplary assay methods include direct morphological analysis, phenotypic analysis by flow cytometry, antigen capture measurable by FITC-Dextran uptake, and induction of allogeneic naïve CD4+ T cells measurable by thymidine incorporation. This in vitro diagnostic assay includes a known set of standards in order to classify the results obtained with the sample of serum obtained from the patient. Briefly, serum from a normal patient, i.e., a patient known not to be suffering from an autoimmune disease is run through the assay and the results obtained are used as the standard indicative of low risk for developing an autoimmune disease. Similarly, serum from a patient known to have an autoimmune disease, such as SLE, is taken and used in the assay and the results obtained are used as the standard indicative of high risk for developing an autoimmune disease. Patient serum which supports a high degree of monocyte differentiation to dendritic cells that can be blocked by type I interferon, is considered to place the patient at high risk for developing an autoimmune disease. The "high degree" of monocyte differentiation is determined by comparing the amount of monocyte differentiation in the assay using the patient's serum with the standards previously established for high risk, low risk and any other middle risk values. Each level of risk for developing an autoimmune disease is associated with a level of monocyte differentiation observed in the assay. If the patient serum does not support a high degree of monocyte differentiation to dendritic cells that can be blocked by type I interferon, then the patient's level of risk for developing an autoimmune disease is little or no risk. For a patient diagnosed with an autoimmune disease, periodic evaluation of the patient's serum in this assay provides a method to monitor for a disease flare or progression

EXAMPLE 9

TNF Inhibits Type I Interferon Secretion by pDCs

Kadowaki et al. (*J. Exp. Med.* 2000, 192:1785-96) disclose that autocrine IFN-α supports pDCs survival while the autocrine INF-α induces their maturation into mature pDCs, which are unable to produce IFN-α. Thus, studies were performed to determine whether or not adding neutralizing TNF antibodies to cultures of normal pDCs sustained their IFN-α production in response to viral triggering.

For these studies, pDCs were isolated from cultures of CD34+hematopoietic progenitors by flow cytometry sorting of CD11c negative and CD123 positive cells. The isolated pDCs were cultured at a concentration of 50,000 cells per well/200 μL with purified influenza virus (5 μL) and either a control antibody or a neutralizing anti-TNF antibody (primary culture). After 24 hours of primary culture, the plates were centrifuged, supernatants were harvested, and the cells were re-cultured in fresh medium with the fresh dose (5 μL) of flu virus (secondary culture). After additional 24 hours of secondary culture, the supernatants were harvested and evaluated for the presence of IFN-α levels.

Figure 14B:
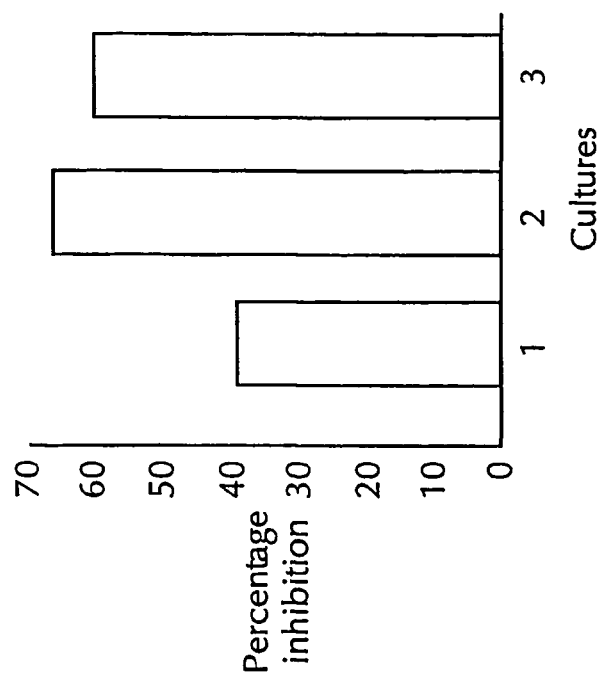
FIGS. 14A-14C are graphic illustrations showing TNF regulation of IFN-α secretion by plasmacytoid DCs (pDCs).
Figure 14A:
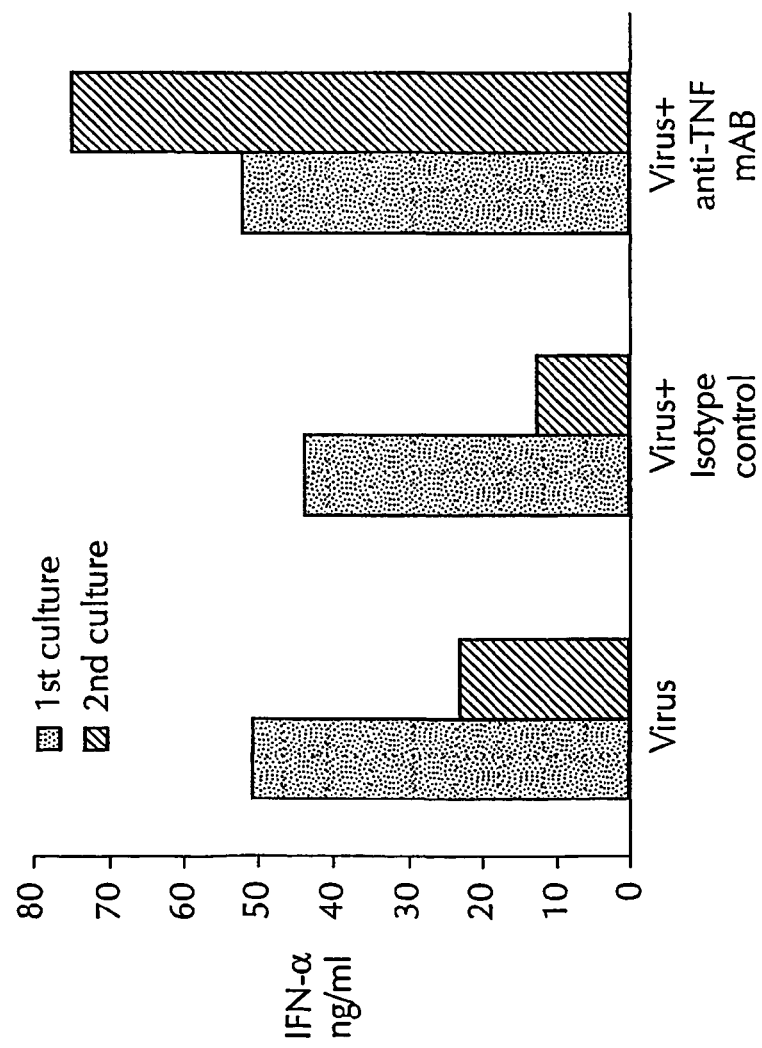
Figure 14C:
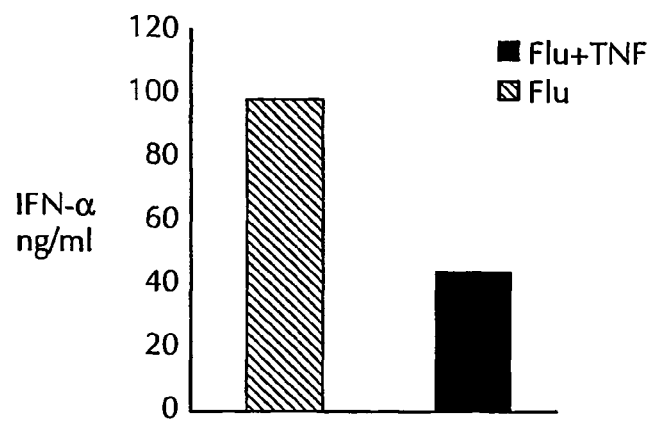

FIGS. 14A-14C show TNF regulation of IFN-α secretion by plasmacytoid DCs (pDCs). Purified DCs generated in vitro by culturing CD34+ hematopoietic progenitor cells with Flt3L (100 ng/mL) and thrombopoietin (TPO) (30 ng/mL), are cultured at a concentration of 50,000 cells per well with purified influenza virus (5 μL) with either a control antibody (5 μg/mL) or with neutralizing anti-TNF antibody (5 μg/mL) or with exogenous TNF (100 ng/mL) (primary culture). After 24 hours of culture, the plates were centrifuged, supernatants were harvested and the cells were re-cultured in fresh medium with the fresh dose of influenza virus (secondary culture). After an additional 24 hours of culture, the supernatants were harvested for the evaluation of IFN-α levels. As shown in FIG. 14A, adding neutralizing anti-TNF antibody resulted in a 3-fold increased release of IFN-α in secondary cultures. Conversely, adding TNF resulted in up to 70% inhibition of IFN-α release in primary cultures of pDCs (see FIG. 14B). As illustrated in FIG. 14C, the concentration of IFN-α in the primary culture supernatants was decreased from 100 ng/mL to 40 ng/mL.

Figure 16:
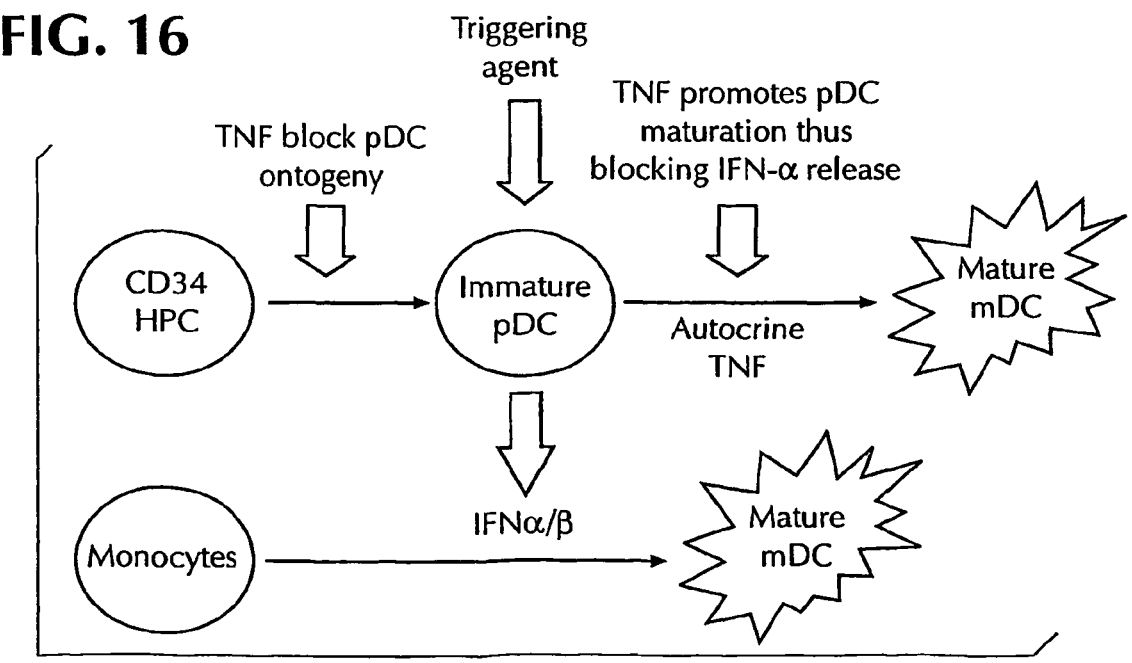
FIG. 16 is a schematic illustration showing pathways in plasmacytoid DC ontogeny that can be inhibited by exogenous TNF which functions as an interferon antagonist.

This study provides the non-limiting theory summarized in FIG. 16 of how immature pDCs can be blocked from secreting IFN-α by incubation in TNF (or an agonistic anti-TNF receptor binding agent). The pDCs incubated with TNF are thus promoted to become mature pDCs, which do not secrete IFN-α.

EXAMPLE 10

TNF Inhibits pDC Ontogeny

Studies were next performed to determine whether the effect of TNF on pDC is restricted to their maturation/IFN-α production or whether TNF, a major pro-inflammatory cytokine involved in the regulation of myeloid dendritic cells differentiation, also affects differentiation of pDCs from hematopoietic progenitors. For these studies, CD34+

CD45RA− hematopoietic progenitors were sorted to over 90% purity by flow cytometry and subsequently cultured in the presence of Flt3L (100 ng/mL, R&D), thrombopoietin (TPO, 30 ng/mL, R&D), and either interleukin-6 (IL-6, 25 ng/mL, R&D), or tumor necrosis factor (TNF, 100 ng/mL, R&D), in the first week of culture at a density of between $2/5 \times 10^5$ to $5 \times 10^5$/well. Thereafter, the cells were washed and cultured for about an additional 3 weeks with Flt3L (100 ng/mL) only.

Figure 15:
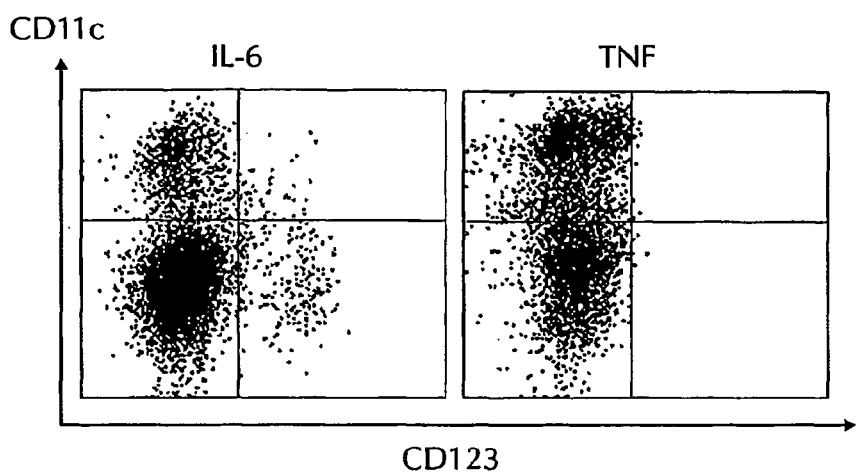
FIG. 15 is a graphic illustration of a flow cytometry experiment which shows that TNF blocks plasmacytoid DCs' differentiation in favor of myeloid DCs. The figure depicts TNF inhibition of the generation of pDC from CD34+ hematopoietic progenitor cells. CD34+CD45RA– hematopoietic progenitors were cultured in the presence of Flt3L (100 ng/mL), TPO (30 ng/mL) and either IL-6 (25 ng/mL) or TNF 100 ng/mL in the first week of culture. Thereafter, the cells were washed and cultured for additional 3 weeks with Flt3L only (100 ng/mL). pDC differentiation was determined by flow cytometry analysis of cell surface marker expression with pDC being identified by CD11c negative CD123 positive staining.

FIG. 15 shows results of a flow cytometry experiment which shows that TNF blocks plasmacytoid DCs' differentiation in favor of myeloid DCs. pDC differentiation was determined by flow cytometry analysis of cell surface marker expression with pDC being identified by CD11c negative CD123 positive staining. Thus, adding TNF in the first week resulted in a complete inhibition of progenitor cell differentiation into CD123+CD11c− pDCs and skewed differentiation towards CD123-DC11c+ myeloid DCs. Thus, TNF and/or agonistic anti-TNF receptor antibodies, both of which stimulate the TNF receptor on the progenitor cells, block the pDCs' differentiation and redirect progenitor cells towards mycloid DCs differentiation.

This study provides the non-limiting theory shown on FIG. 16 of how IFN-α production and secretion can be blocked by exposing progenitor cells to TNF (or an agonistic anti-TNF receptor binding agent). Such exposure leads to the inhibition of the development of pDCs that can make interferon and therefore blocks interferon production and secretion.

EXAMPLE 11

The Level of Flt3L is Increased in Serum from Subjects Suffering from SLE

As described in the above examples, unabated DC induction is believed to drive the devastating autoimmune response in SLE and, as described herein, may be controlled by targeting IFN-α and Flt3L together. However, other cytokines, which are termed herein as "DC-poietins", can mobilize and/or activate DCs to differentiate into antigen presenting cells in vivo. This mobilization or activation of DCs can occur in many different ways. For example, such DC-poietins can increase differentiation of preDC cells into mature dendritic cells which can go on to increase an immunogeneic response and worsen the autoimmune responses. As another example, the DC-poietins can increase the actual generation of newly matured DCs which contribute to the autoimmune responses in the subject, or the DC-poietins can increase the activity of mature DCs.

One non-limiting DC-poietin is the Flt3L, which has been shown to mobilize large numbers of DCs, both myeloid and plasmacytoid, in vivo in human and mouse models (Maraskovsky et al (1997) *Adv. Exp. Med. Biol.* 417:33-40; (1996) *J. Exp. Med.* 184(5):1953-62; (2000) *Blood* 96(3):878-84). Furthermore, as shown in the present invention, culturing CD34+ hematopoietic stem cells with Flt3L yields not only plasmacytoid DCs but also CD11c+ myeloid DCs as well as monocytes.

Figure 17:
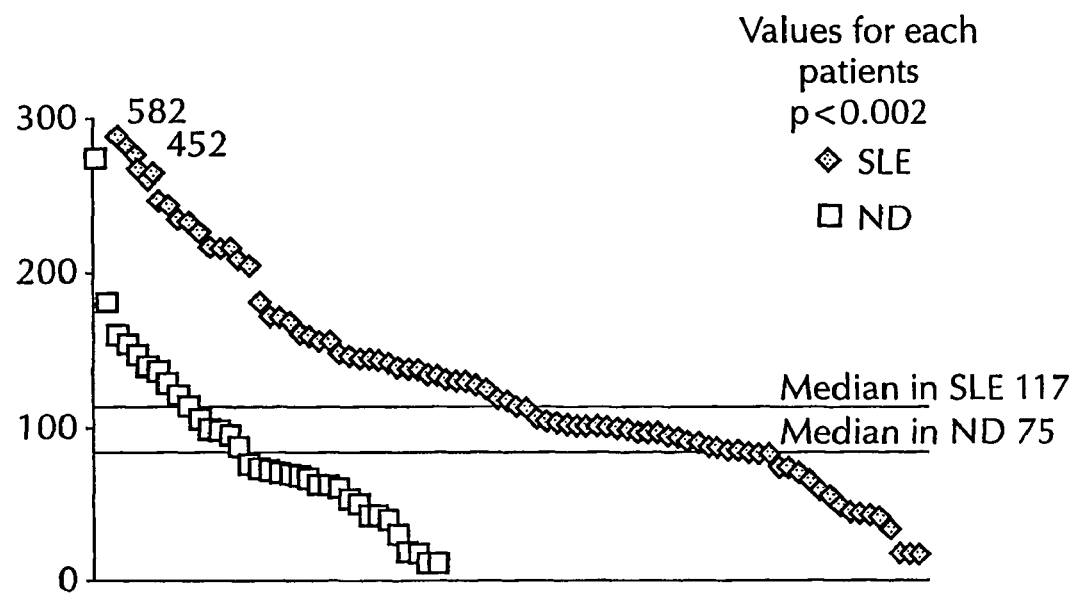
FIG. 17 is a graphic illustration showing increased levels of Flt3L (in pg/mL) in serum of patients with SLE.

Serum levels of Flt3L in patients with SLE (83 blood samples) as well as in healthy controls (35 blood samples) was determined using commercially available ELISA (R&D). As shown in FIG. 17, SLE patients have significantly higher serum levels of Flt3L (p<0.002) ranging from <12.5 to 582 pg/mL of serum, than that measured in serum taken from healthy subjects. 83 blood samples from SLE patients and 35 blood samples from healthy patients (healthy controls) were tested using a commercially available ELISA. The differences in levels of Flt3L in the serum samples are statistically significant using both parametric and non-parametric analysis.

EXAMPLE 12

Serum Levels of Flt3L Correlate with Autoimmune Disease Activity

Figure 18:
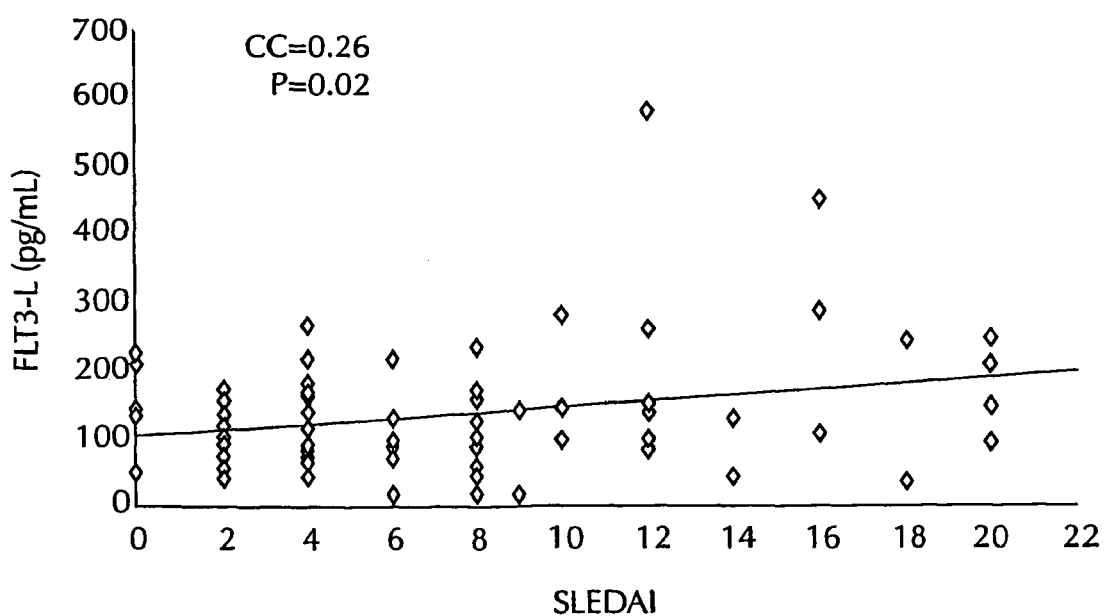
FIG. 18 is a graphic illustration showing correlation of serum levels of Flt3L in SLE patients and disease activity as measured by the SLEDAI. Statistical significance was determined by linear regression and Pearson analysis.

It was determined that serum levels of Flt3L correlate with disease activity as measured by the SLE Disease Activity Index (SLEDAI). As shown in FIG. 18, there was a significant positive correlation (p=0.02), indicating that those individuals with high serum levels of Flt3L also had displayed high SLE disease activity. Therefore, the occurrence of elevated levels of Flt3L in the serum is an indicator of autoimmune risk or active autoimmune disease in a subject.

EXAMPLE 13

Flt3L Permits Monocyte Differentiation into DCs

Figure 19A:
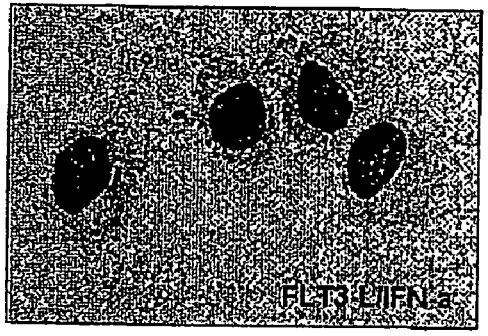
FIGS. 19A-19D are photographic illustrations that show monocytes cultured with media supplemented with Flt3L differentiate into cells with DC morphology.
Figure 19B:
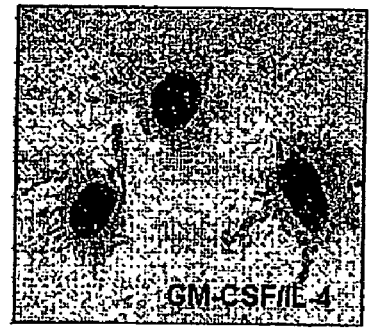
Figure 19C:
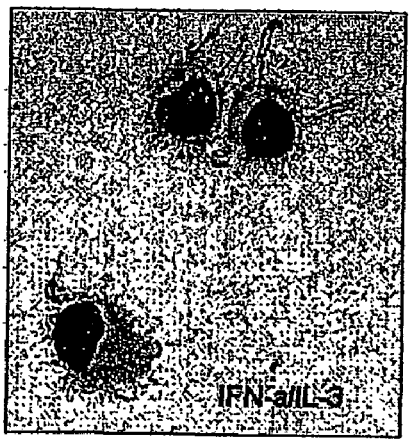
Figure 19D:
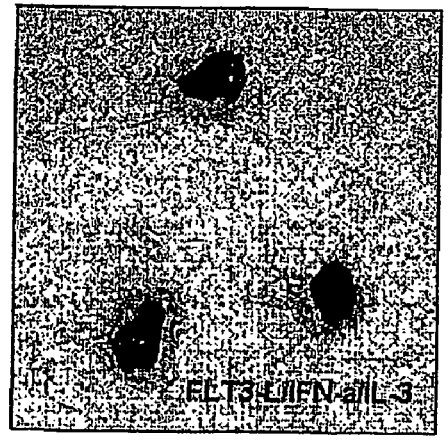
Figure 20:
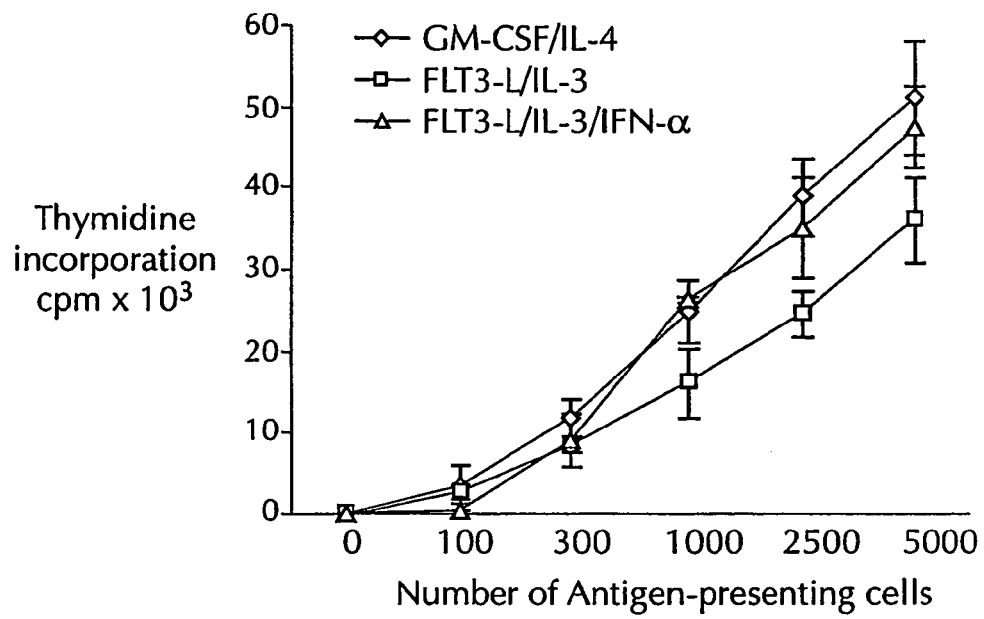
FIG. 20 is a graphic illustration showing that monocytes cultured with media supplemented with Flt3L (100 ng/mL) are able to prime naive CD4+ T cells.
Figure 21:
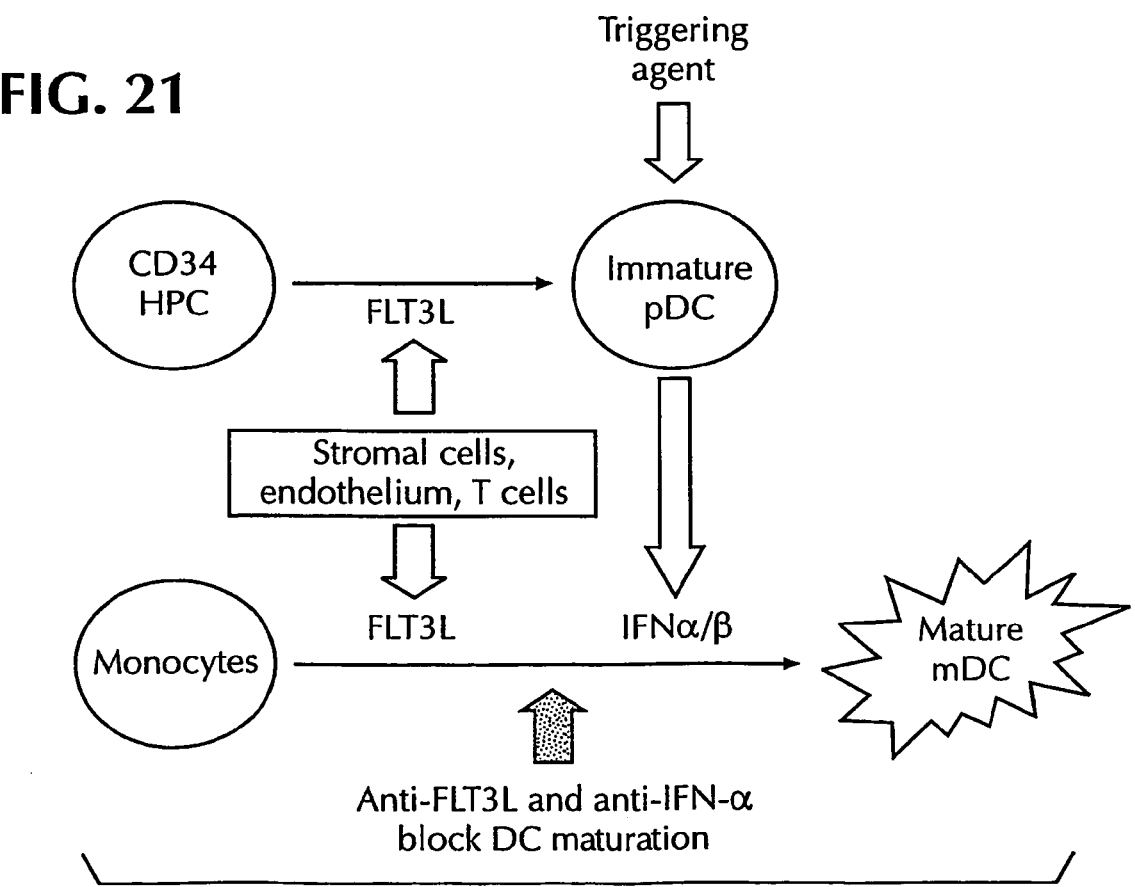
FIG. 21 is a schematic illustration which shows several pathways in the development and differentiation of subsets of DC which can be altered by blocking the activity of Flt3L and IFN-α.
Figure 22:
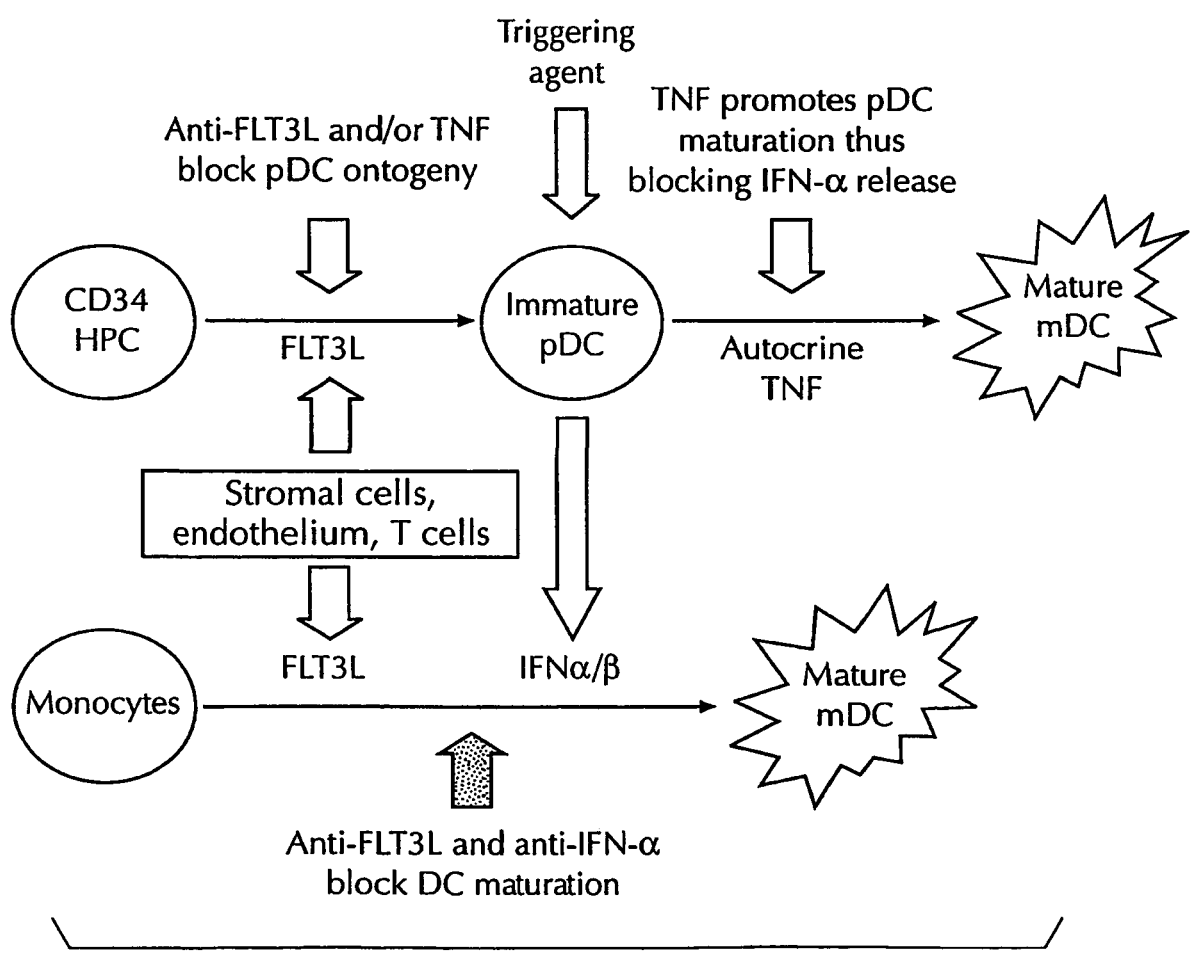
FIG. 22 is a schematic illustration showing the interplay between cytokines and DCs in SLE and identifying cytokines and/or cellular targets which are intended for therapeutic compositions of the invention herein.

Monocytes isolated from healthy donors' peripheral blood mononuclear cells (PBMCs) were either isolated by positive selection using CD14 beads or enriched by adherence and subsequently cultured for 2 days in a complete culture medium (RPMI1640 supplemented with 10% heat-inactivated fetal calf serum) with Flt3L (100 ng/mL) and IL-3 (10 ng/mL) and/or IFN-α (1000 U/mL). Control cultures were carried out with GM-CSF and IL-4. FIG. 19A shows cells cultured with Flt3L/IFN-α (1000 u/mL). FIG. 19B shows cells cultured with GM-CSF (100 ng/mL)/IL-4 (5 ng/mL). FIG. 19C shows cells cultured with IFN-α (1000 u/mL)/IL-3 (10 ng/mL). FIG. 19D shows cells cultured with Flt3L/IFN-α (1000 u/mL)/IL-3 (10 ng/mL). After 2 days of culture, cytospun monocytes were stained with Giemsa. Thus, monocytes cultured with Flt3L and IFN-α differentiate into cells displaying features of DCs as determined by morphology (FIGS. 19A-19D), phenotype (CD14 low, DC-SIGN+, CD40+, HLA-DR+, CD11c+) and function, i.e., the capacity to induce proliferation of allogeneic CD4+ T cells which is a hallmark of dendritic cell function (FIG. 20). In FIG. 20, $10^5$ purified allogeneic CD4+ T cells were cultured for 5 days with graded numbers of antigen presenting cells (horizontal axis). T cell proliferation was measured by thymidine incorporation (vertical axis, cpm×$10^3$) following culture with media supplemented with Flt3L. FIG. 21 shows a diagram summarizing several pathways in the development and differentiation of subsets of DC which can be altered by blocking the activity of Flt3L and IFN-α. These therapeutic targets include 1) differentiation pathway from hematopoietic progenitor cells into pDC, which can be blocked either by TNF or by Flt3L antagonist or by a combination of both TNF and Flt3L antagonist with the end result being inhibited interferon production through the inhibition of the differentiation of cells that can make interferon, 2) pDCs maturation pathway, which can be accelerated by TNF with the end result being that pDCs become non-interferon producing cells thus decreasing levels of interferon, 3) differentiation pathway from monocytes to dendritic cells, which can be blocked by an interferon antagonist or by a Flt3L antagonist or by a combination of interferon antagonist and a Flt3L antagonist, with the end result being inhibited differentiation of dendritic cells that are otherwise able to capture and present apoptotic cells and drive autoimmune disease by inducing the differentiation of autoreactive B cells and autoreactive T cells.

EXAMPLE 14

Neutralizing Flt3L in SLE Serum Inhibits SLE Serum-Induced Monocyte Differentiation into Dendritic Cells Monocytes are cultured with serum obtained from a patient with SLE. An effective amount of a monoclonal antibody which specifically binds Flt3L (anti-Flt3L monoclonal antibody) is added, at the saturating concentration, I.e., a concentration ranging between about 1-10 fold molar excess, to the monocyte cell culture under suitable culture conditions for monocyte differentiation. After three days of incubation, a lower number of monocytes had differentiated into DCs than in an identical monocyte culture which had not received the monoclonal antibody. Therefore, the monoclonal antibody to Flt3L which neutralizes the activity of Flt3L in the culture inhibits SLE-induced monocyte differentiation into DCs.

EXAMPLE 15

Addition of a Composition of a Flt3L Antagonist and an Interferon Antagonist to Monocytes Grown in SLE Serum Inhibits Monocyte Differentiation Int Antigen Presenting DCs A method for treating an autoimmune disease in a subject is exemplified herein whereby a therapeutic composition of the invention is administered to the subject in order to reduce or inhibit the generation of antigen presenting cells which cause the stimulation of autoreactive T cells and of autoreactive B cells which produce auto-antibodies in the subject.

A therapeutic composition is prepared with an amount of (a) an anti-Flt3L monoclonal antibody and (b) an amount of an anti-IFN-α monoclonal antibody which is equal to about 1-10 fold the level of Flt3L and IFN-α, respectively, in the serum of the patient to be treated. Methods for preparing monoclonal antibodies to Flt3L are known, for example one such method is in Example 6 of U.S. Pat. No. 5,843,423, "Methods of Stimulating hematopoietic cells with flt3-ligand." Methods for preparing monoclonal antibodies to IFN-α are known and, for example, some such methods are set out in U.S. Pat. No. 5,919,453.

Serum can be obtained from the subject with the autoimmune disease and tested to insure that sufficient levels of Flt3L and IFN-α are present in the serum to warrant the administration of the therapeutic composition.

The composition is administered daily via an injection or via an intravenous delivery method to insure a serum level of the two elements of the composition is within a range from about 1 to about 10 fold molar excess of Flt3L and/or IFN-α. Monitoring of the subject's condition can be carried out throughout the treatment period so as to determine the level of generation of APCs. Existence of DCs in the subject's serum is monitored throughout the treatment. The treatment is terminated when the symptoms of the autoimmune disorder subside and it is undertaken again when the levels of Flt3L and/or IFN-α show an increasing trend over two consecutive blood analyses and/or when the symptoms of the autoimmune disorder worsen.

What is claimed is:

1. A method of inhibiting differentiation of $CD14^+$ monocytes into dendritic cells capable of antigen presentation, comprising administering an effective amount of (a) at least one interferon antagonist that reduces activity of a type I interferon, wherein the interferon antagonist comprises an anti-IFN-α antibody or an antigen-binding fragment thereof, and (b) at least one Flt3 ligand (Flt3L) antagonist that reduces activity of a Flt3L, wherein the Flt3L antagonist comprises an anti-Flt3L antibody or an antigen-binding fragment thereof, thereby inhibiting $CD14^+$ monocyte differentiation into dendritic cells.

2. The method of claim 1, wherein the anti-IFN-α antibody is a monoclonal antibody, a chimeric antibody, an anti-idiotypic antibody, a humanized antibody, a primatized antibody, or any combination thereof.

3. The method of claim 1, wherein the interferon antagonist and the Flt3L antagonist are part of one molecule.

4. The method of claim 1, wherein the effective amount of the interferon antagonist comprises from about 1 to about 10 fold molar excess of interferon.

5. The method of claim 1, wherein the effective amount of the Flt3L antagonist comprises from about 1 to about 10 molar excess of Flt3L.

6. The method of claim 1, wherein the anti-Flt3L antibody is a monoclonal antibody, a chimeric antibody, an anti-idiotypic antibody, a humanized antibody, a primatized antibody, or any combination thereof.

* * * * *